United States Patent [19]
Giannos et al.

[11] Patent Number: 6,068,853
[45] Date of Patent: May 30, 2000

[54] TEMPORALLY CONTROLLED DRUG DELIVERY SYSTEMS

[75] Inventors: Steven Andrew Giannos, Nanuet, N.Y.; Steven Minh Dinh, Ridgefield, Conn.; Bret Berner, El Granada, Calif.

[73] Assignee: Novartis Corporation, Summit, N.J.

[21] Appl. No.: 08/542,580

[22] Filed: Oct. 13, 1995

Related U.S. Application Data

[63] Continuation-in-part of application No. 08/226,917, Apr. 13, 1994, abandoned.

[51] Int. Cl.⁷ .............................. A61K 9/00; A61K 9/70
[52] U.S. Cl. ...................... 424/449; 424/447; 424/448; 604/890.1
[58] Field of Search .................. 424/422, 451, 424/464, 473, 447, 448, 449; 514/947, 970; 604/890.1

[56] References Cited

U.S. PATENT DOCUMENTS

| | | |
|---|---|---|
| 3,598,122 | 8/1971 | Zaffaroni . |
| 3,916,899 | 11/1975 | Theeuwes et al. . |
| 3,996,934 | 12/1976 | Zaffaroni . |
| 4,326,525 | 4/1982 | Swanson et al. . |
| 4,439,195 | 3/1984 | Swanson et al. . |
| 4,455,143 | 6/1984 | Theeuwes et al. . |
| 4,597,961 | 7/1986 | Etscorn . |
| 4,743,249 | 5/1988 | Loveland . |
| 4,756,710 | 7/1988 | Bondi et al. . |
| 4,781,924 | 11/1988 | Lee et al. ................ 424/449 |
| 4,797,284 | 1/1989 | Loper et al. ............ 424/449 |
| 4,837,027 | 6/1989 | Lee et al. ................ 424/449 |
| 4,911,707 | 3/1990 | Heiber et al. ........... 424/449 |
| 4,917,676 | 4/1990 | Heiber et al. ........... 424/449 |
| 4,917,895 | 4/1990 | Lee et al. ................ 424/448 |
| 5,064,654 | 11/1991 | Berner et al. . |
| 5,073,539 | 12/1991 | Mazzenga et al. . |
| 5,196,126 | 3/1993 | O'Dowd .................. 210/754 |
| 5,284,660 | 2/1994 | Lee et al. ................ 424/449 |
| 5,342,623 | 8/1994 | Enscore et al. . |
| 5,364,630 | 11/1994 | Osbonne et al. . |
| 5,423,739 | 6/1995 | Phipps et al. ........... 604/20 |
| 5,525,356 | 6/1996 | Jevne et al. ............. 424/484 |

FOREIGN PATENT DOCUMENTS

| | | |
|---|---|---|
| 0197504 | 10/1986 | European Pat. Off. . |
| 9202464 | 2/1992 | WIPO . |

OTHER PUBLICATIONS

Hrushesky; Journal of Controlled Release 19 (1992) 363–368 Temporally Optimizable Delivery Systems:Sine-qua Non for the Next Therapeutic Revol .

Lemmer; Advanced Drug Delivery Reviews, 6 (1991) 83–100; "Implications of Chronopharmacokinetics for Drug Delivery . . . ".

Kost et al; Advanced Drug Delivery Reviews, 6 (1991) 19–50; "Responsive Polymeric Delivery Systems".

Siegel et al; Proceed. Intern. Symp. Control. Rel. Bioact. Mater. 20 (1993) 49–"Strategy for Sustained Periodic Drug Delivery."

(List continued on next page.)

*Primary Examiner*—Robert H. Harrison
*Attorney, Agent, or Firm*—Stephen G. Kalinchak; William K. Wissing

[57] ABSTRACT

A delivery mechanism and device for the passive periodic release of a drug or an active ingredient which avoids the need for external power sources and/or electronic controllers. By taking advantage of oscillating chemical systems, one can change the state, i.e. the pH, of a solution, a drug, enhancer or solubilizer resulting in oscillating the ability of an active ingredient to be delivered transdermally. The pH of a solution can be oscillated over a range of pH values from 2 to 10 by the reduction and oxidation (redox) reactions of salts, such as permanganates, iodates, sulfates, chlorates, or bromates. Upon activation, the delivery system conditions begin to oscillate and with it, the delivery of the active agent oscillates.

14 Claims, 27 Drawing Sheets

OTHER PUBLICATIONS

Zhabotinskii; in Oscillations & Traveling Waves in Chemical Systems John Wiley & Sons (New York 1983); "The Early Period of Systematic Studies of Oscillations and Waves in Chemical Systems".

Rabai, et al; Acc. Chem. Res. 23, 258–263 (1990); "Design of pH–Regulated Oscillators".

Epstein et al; in "Oscillations & Traveling Waves in Chemical Systems"; John Wiley & Sons, New York 1983; "Halogen Based Oscillators in a Flow Reactor." p. 257–286.

Troy; in "Oscillations & Traveling Waves in Chemical Systems"; John Wiley & Sons, New York (1983) p. 145–170. "Mathematical Analysis of the Oregonator Model of the Belousov–Zhabotinskii Reaction."

Luo et al., J. Am. Chem. Soc. 1991, 113, p. 1518–1522, "A General Model for pH Oscillators".

Rabai et al; J. Am. Chem. Soc. 114 (1992) 1529–1530; "pH Oscillators in a Semibatch Reactor."

Rabai et al; J. Phys. Chem. 92 (1988) 4831–4835; "High Amplitude Hydrogen Ion Concentration Oscillation in the Iodate–Thiosulfate–Sulfite System Under Closed Conditions."

Field; Journal of Chem. Ed. 49, No. 5, May 1972, 308–311; "A Reaction Periodic in Time and Space."

Field et al; J. of Chem. Ed. 66, No. 3, Mar. 1989, 195–204; "Oscillating Chemical Reactions and Nonlinear Dynamics."

Rabai, et al; J. Phys. Chem. 92 (1988) 2804–2807; "Exotic Kinetic Phenomena and Their Chemical Explanation in the Iodate–Sulfite–Thiosulfate System".

Gooda et al; J. of Polym. Sci. Part A, 39 (1992) 1549–1557; "New Water Soluble Polymers and Copolymers by Interaction of Polyelectrolytes with Formamide."

Gooda et al; Macromolecules 25 (1992) 4215–4217; "Dilute Solution Properties of a New Water–Soluble Polymer."

Orban et al; J. Am Chem. Soc. 109 (1987) 101–106 "Chemical Oscillators in Group VI A: The Cu(11)–Catalyzed Reaction Between Hydrogen Peroxide and the Thiosulfate Ion."

Maselko, et al; J. Phys Chem 93 (1989) 2774–2780 "Regular and Irregular Spatial Patterns in an Immobilized–Catalyst Belousov–Zhabotinsky Reaction."

Lengyel et al; Science, vol. 251, 650–652 (1991) "Modeling of Turing Structures in the Chlorite–Iodide–Malonic Acid–Starch Reaction System."

Agladze et al; J. Phys. Chem. 96 (1992) 2400–2403 "Turing Patterns in Confined Gel and Gel Free Media."

Epstein et al; J. Phys. Chem. 96 (1992) 5852–5856 "Kinetics & Mechanism of the Chlorite–Thiourea Reaction in Acidic Medium."

Morimoto et al; Chem. Pharm. Bull. 39(9) 2412–2416 (1991); "Effect of Ion Species and Their Concentration on the Iontophoretic Transport of Benzoic Acid Through Poly-(Vinyl Acetate) Membrane."

Maurin et al; J. of Pharmaceutical Sciences, vol. 81, No. 1, Jan. 1992, 79–84; "Mechanism of Diffusion of Monosubstituted Benzoic Acids Through Ethylene–Vinyl Acetate Copolymers."

Mohan et al; Drugs of the Future 18(4):351–358 1993; "Sulfonic Acid Derivatives as Selective Anti–HIV–1 Agents."

Elswirth et al; J. Phys. Chem. 95 (1991) 1294–1299; "Operational Procedure Toward the Classification of Chemical Oscillators."

Palmer et al; Drugs 44(3) 498–529 (1992).

Mohan; Drug DeV. Res. 29:1–17 (1993).

INPUT
    DRUG CONCENTRATION PROFILE IN SYSTEM, $C(t)$.

OUTPUT
    FLUX OF DRUG ACROSS MEMBRANE(S), $j(t, x=0)$.

INPUT-OUTPUT $$j(t,x=0) = -\frac{2KD}{\lambda l} \sum_{n=1}^{\infty} (-1)^{n+1} n^2 \left[ \int_0^t C(\tau) e^{n^2 t/\lambda} d\tau \right] e^{-n^2 t/\lambda}$$

WHERE, $$\lambda = \frac{6}{\pi^2} \quad t_L = \frac{l^2}{\pi^2 D}$$

OUTPUT-INPUT $$C(t) = -\frac{l}{KD} L^{-1} \left\{ \frac{j(s,x=0)}{\sqrt{sl^2/D}} \sinh(sl^2/D) \right\}$$

WHERE, $L^{-1}$ IS THE INVERSE Laplace TRANSFORM OPERATOR.

FIG.1B

CONSTANT SOURCE OF INPUT $$j(t,x=0) = -\frac{2KDC_o}{l}\sum_{n=1}^{\infty}(-1)^{n+1}\left[1-e^{-n^2t/\lambda}\right]$$

AT STEADY-STATE, $$j_{ss}(x=0) = -\frac{KDC_o}{l}$$

SINUSOIDAL INPUT [$C(t) = C_{max}\sin(\omega t)$]

$$\underbrace{\frac{|j(t,x=0)|}{2KDC_{max}} = \sum_{n=1}^{\infty}(-1)^{n+1}n^2\left\{\frac{1}{(n^4+\lambda^2\omega^2)^{1/2}}\sin\left[\omega t - \tan^{-1}\left(\frac{\lambda\omega}{n^2}\right)\right] + \frac{\lambda\omega}{(n^4+\lambda^2\omega^2)}e^{-n^2t/\lambda}\right\}}_{}$$

dimensionless
flux forced oscillation    diffusion

SAME FREQUENCY
PHASE SHIFT
MEMBRANE CONTROLLED: $\lambda\omega >> 1$
INPUT CONTROLLED: $\lambda\omega << 1$ $$\omega \alpha \frac{1}{P}$$

FIG.1C

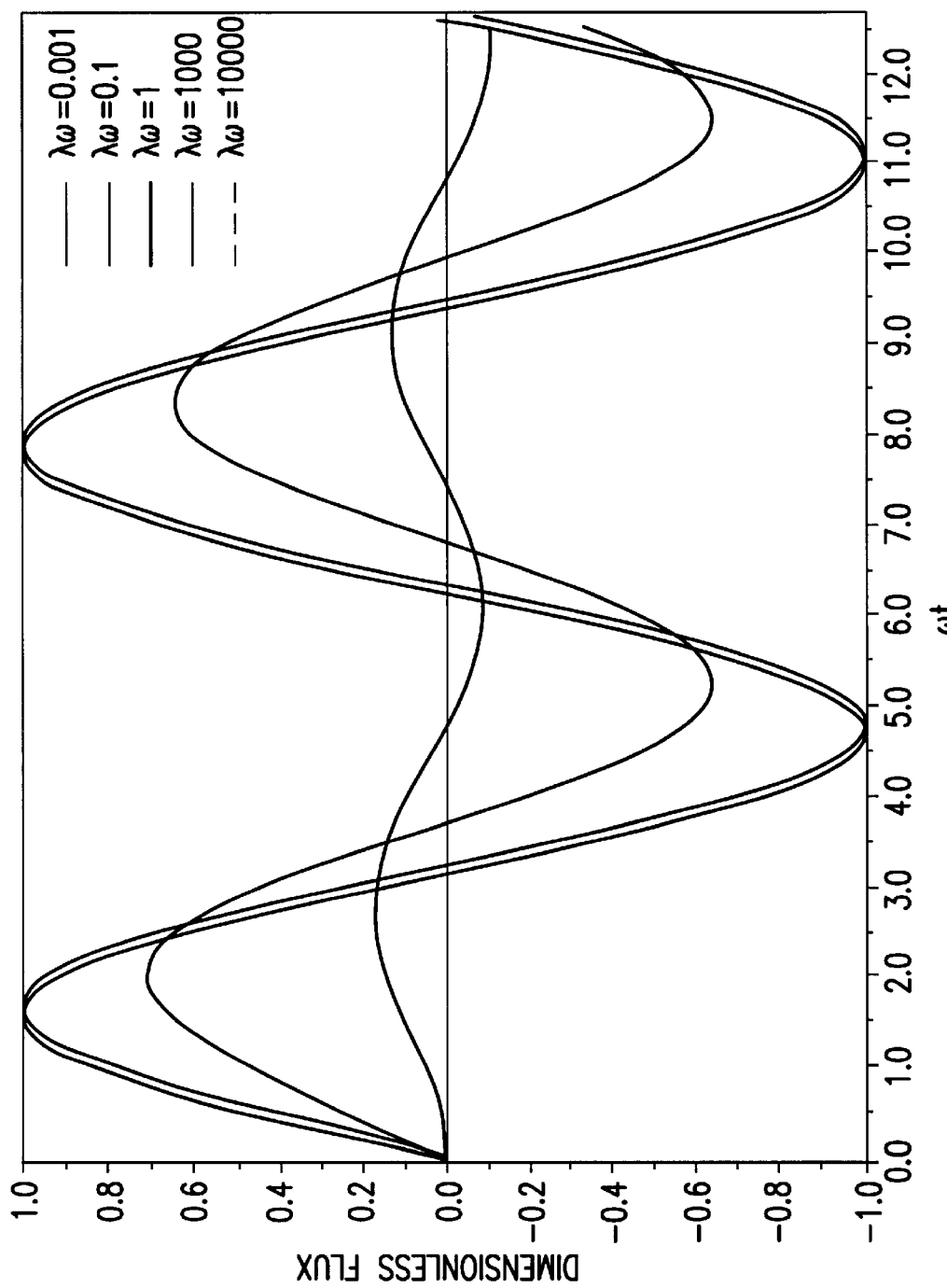

MODEL MECHANISM:

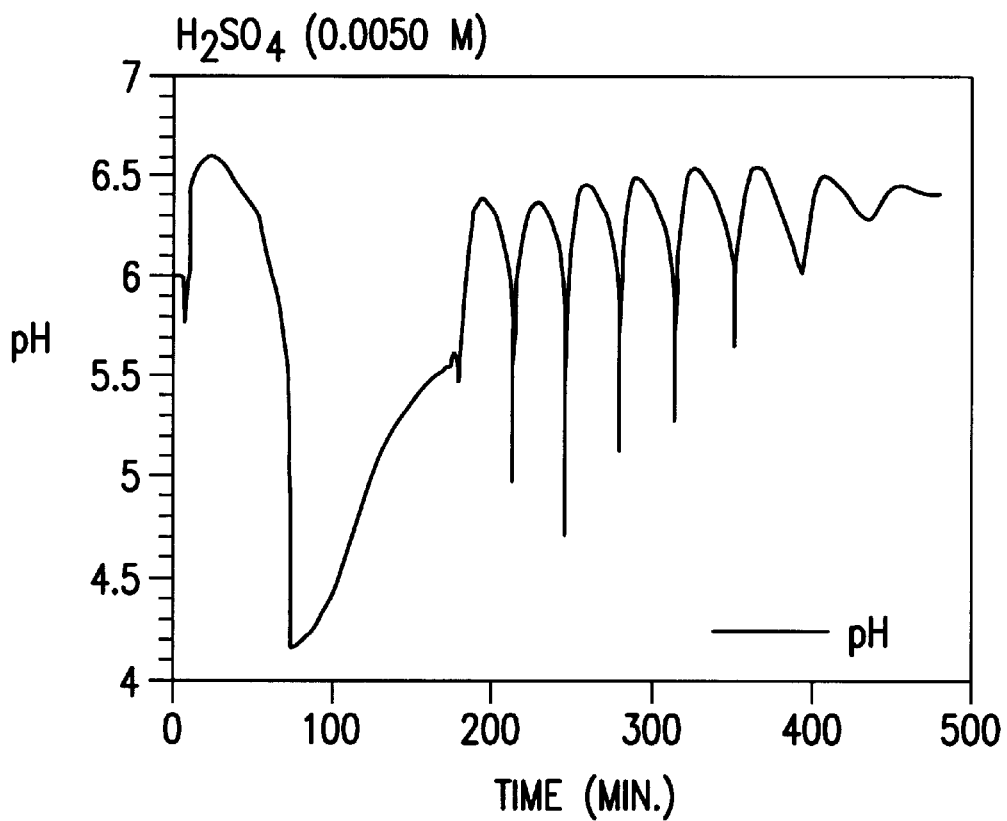
FIG.5A
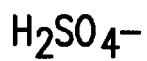
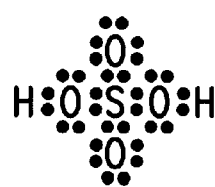
FIG.5A-1

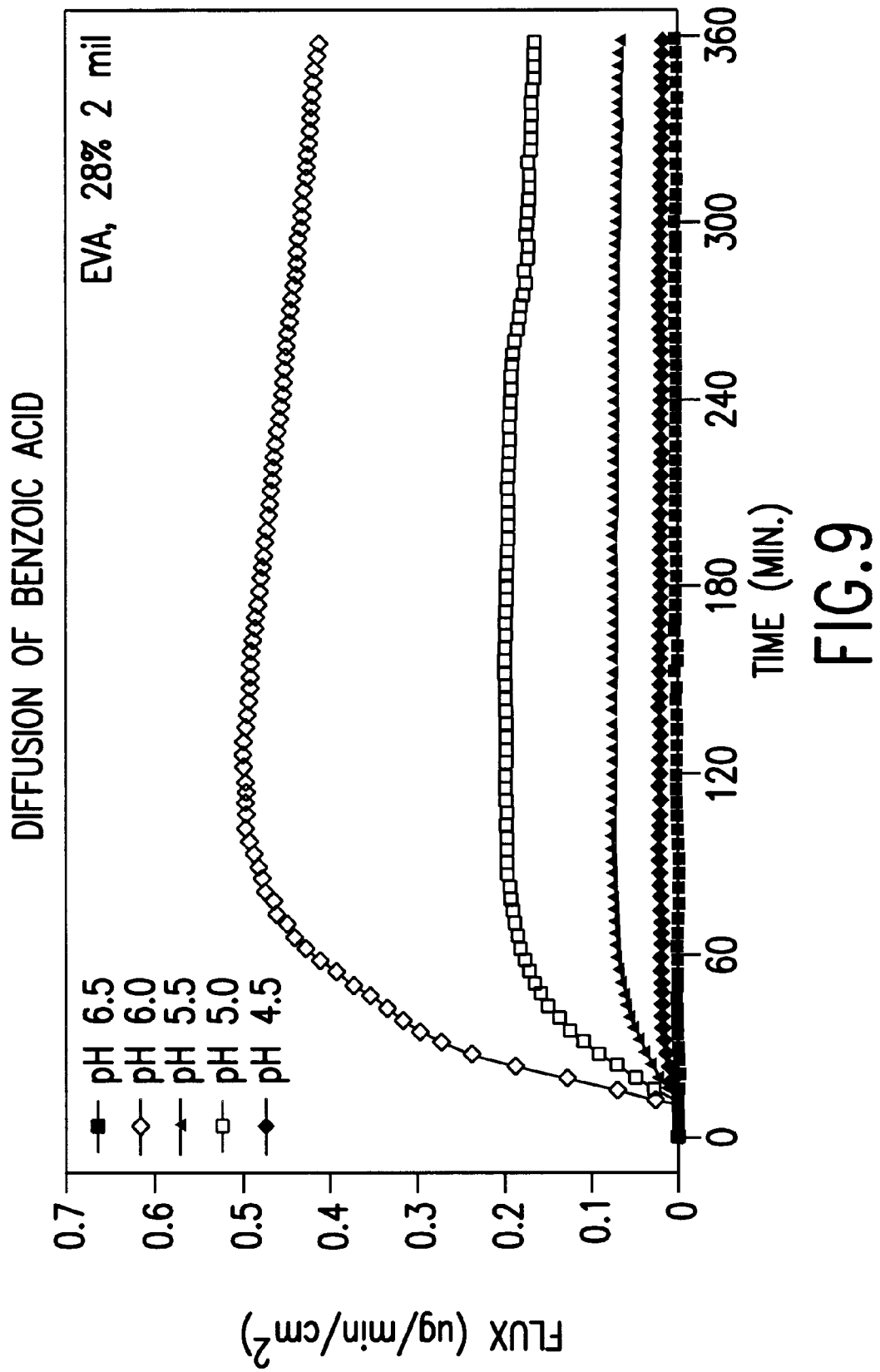

PAMPS
$Na_2SO_3$
$Na_2S_2O_3$
DRUG

TEMPORALLY CONTROLLED DRUG DELIVERY SYSTEMS

This application is a CIP of Ser. No. 08/226,917 filed Apr. 13, 1994 ABN.

FIELD OF THE INVENTION

This invention relates to the application of chemical oscillating reactions to active agent delivery systems so as to modulate the delivery of such active agent from the system. The invention further relates to overcoming active agent tolerance which may be experienced from continuous administration. The invention also relates to the field of chronobiology in that the invention systems can be designed to modulate active agent delivery in accordance with biological rhythms.

BACKGROUND OF THE INVENTION

The emerging interest in chronopharmacology demonstrates the fact that biological rhythms are an important aspect of clinical pharmacology and should be taken into account when evaluating drug delivery systems (Hrushesky, W., J.Cont. Rel. 19:363 (1992) and Lemmer, B., Adv. Drug Del. Rev. 6:19 (1991)). Studies indicate that the onset of certain diseases show strong circadian temporal dependency. This has led to the need for timed patterning of drug delivery as opposed to constant drug release. Currently, drug delivery modulation is being accomplished by external means, such as ultrasonic modulation, magnetic modulation and iontophoresis (Kost, J., Langer, R., Adv. Drug Del. Rev. 6:19 (1991)). Self-regulated delivery systems, only recently being discussed, are generally based on the enzymatic triggering of a functionalized polymer (Kost et al., above). A theoretical model of an oscillating chemical reaction of a membrane for periodic drug delivery has recently been published by Siegel and Pitt (Siegel, R. A. and Pitt, C. G., Proceed. Intern. Symp. Control Rel. Bioact. Mater., 20:49 (1993)). The present approach is for the passive periodic release of a drug or active ingredient utilizing oscillating chemical reactions, thus avoiding the need for external power sources and/or electronic controllers. In other words, once the oscillation reaction is begun, the oscillation reaction, and thereby the delivery of the active agent, is driven by the free energy of the system.

Chemical oscillating reactions have been known for about one hundred years. The most extensively investigated oscillator, the Belousov-Zhabotinskii (BZ) reaction, has been used as a model for studying a wide variety of temporal and spatial instabilities in chemical systems (Zhabotinskii, A. M. in Oscillations and Traveling Waves in Chemical Systems; Field, R. J., Burger, M., Eds.; Wiley-Interscience: New York, (1983)). BZ systems are generally accepted as the metal ion catalyzed oxidation and bromination of an organic substrate by acidic bromate. In the classic BZ reaction, the pH is fairly stable and not a driving force in the reaction.

The family of pH oscillators consist of those oscillating chemical reactions in which there is a large amplitude change in the pH and in which the pH change is an important driving force rather than merely a consequence or an indicator of the oscillation (Rabai, G. Orban, M. and Epstein, I. R. Acc. Chem. Res. 23:258 (1990) and Luo, Y. and Epstein, I. R. J. Am. Chem. Soc. 113:1518 (1991)). The pH of a solution can be oscillated over a range of pH values from 2 to 10 by the reduction and oxidation (redox) reactions of salts, such as permanganates, iodates, sulfates, chlorates, or bromates. The first pH oscillator, the hydrogen peroxide-sulfide reaction, was discovered only ten years ago. Approximately 14 pH oscillator systems are now known. These include the iodate-sulfite-thiourea system; the iodate-sulfite-thiosulfate system; the iodate-sulfite-ferrocyanide system; the iodate-hydroxylamine system; the periodate-hydroxylamine system; the periodate-thiosulfite system; the hydrogen peroxide-ferrocyanide system; the hydrogen peroxide-thiosulfate-copper(II) system; the hydrogen peroxide-bisulfite-thiosulfate system, the peroxodisulfate-thiosulfate-copper(II) system; the bromite-iodide system; the bromate-sulfite-ferrocyanide system; the bromate-sulfite-thiosulfate system; and the manganese(II)-periodate system. (See Luo and Epstein, above).

The CIMA reaction (chlorite/iodide/malonic acid) (J. Am. Chem. Soc. 1990, 112, 9104–9110) is a redox reaction in which the pH of the solution oscillates in response to, but does not drive, the oscillation reaction.

U.S. Pat. No. 4,756,710 (Bondi et al., 1988) describes a pH-mediated drug delivery system, in which a weakly acidic or basic unionized drug in a transdermal delivery system may be delivered continuously and at a relatively low rate. The pH control described there is to maintain a stable pH, not an oscillating one.

Other typical transdermal systems (without mentioning or utilizing oscillation reactions) which can be modified for use in the present invention include those described in: U.S. Pat. No. 4,781,924; U.S. Pat. No. 3,598,122; U.S. Pat. No. 4,597,961; U.S. Pat. No. 3,996,934; U.S. Pat. No. 4,911,707; U.S. Pat. No. 4,743,249; U.S. Pat. No. 4,917,676; U.S. Pat. No. 5,064,654; U.S. Pat. No. 5,073,539, each of which is incorporated herein by reference.

Oral osmotic systems, such as those embodied in products marketed under the Alza trademark OROS®, typically have a semipermeable membrane which allows fluid into the device to dissolve material internal to the device, thereby creating an osmotic pressure and forcing the dissolved material through an orifice to the external environment. These devices are exemplified by, but not limited to, those in U.S. Pat. No. 4,326,525; U.S. Pat. No. 4,439,195; U.S. Pat. No. 4,455,143; and U.S. Pat. No. 3,916,899, each of which is incorporated herein by reference. These systems can be modified for use in the present invention.

OBJECTS OF THE INVENTION

It is therefore an object of the invention to provide an active agent delivery device which passively and periodically delivers the active agent so as to avoid or minimize active agent tolerance.

It is another object of the present invention to provide a method using chemical oscillators, particularly pH oscillators, to produce the temporal or periodic release of a drug or an active ingredient, particularly by passive means.

It is further an object of the present invention to provide a method using a user activated, transdermal, therapeutic system in which the oscillation reaction components are stabilized during storage and activated when desired, to administer a drug in a temporally controlled manner.

It is still further an object of the present invention to provide improved efficacy of an active agent by controlling the temporal release of the active agent.

It is even further an object of the invention to provide an active agent in a temporal manner in a synchronous pattern with rhythmic body cycles especially for the treatment of diseases associated with disorders of circadian rhythm.

SUMMARY OF THE INVENTION

These and other objects of the invention can be achieved by active agent delivery devices which incorporate oscillating chemical reaction reagents therein, provided the oscillation reaction is not initiated until desired. At least one of the oscillation reagents is separated physically from the remainder of the reactants necessary to initiate the reaction until the reaction is intended to begin. The components are brought together by either the action of the user (as in a user activated transdermal) or in a change of environment (as in the swallowing of an capsule or tablet, insertion of a depot formulation or a suppository, application of a topical or transdermal bandage, exposure to light, etc.).

Once activated, the oscillating reaction results in changes which alter the active agent's ability to leave the delivery form and reach its intended target. In one transdermal embodiment, due to a change in pH (as part of the oscillating reaction, whether or not the pH is the driving force in the reaction), a drug may be rendered charged or uncharged relative to the pKa value of the drug. Since only the uncharged form of a drug can readily permeate across lipophilic membranes, a periodic delivery profile may be obtained.

In another embodiment, the oscillation reaction components are separated by a barrier which is impermeable to at least two oscillation reactants (one retained in each of two compartments), but becomes permeable to at least one of these in the user environment, as in the hydration of a membrane which is impermeable unless hydrated. A recent example of such a membrane is seen in Tamada, et al., Macromol. Rapid Commun. 16: 47–51 (1995).

In a further embodiment, the reactants for a light initiated oscillation reaction are formulated in a suitable form in the absence of initiating actinic radiation. The user exposes the formulation to the appropriate light and uses the activated system.

In still another form, an impermeable membrane separates two components having different portions of the oscillation reaction components. Exposure of the system to moisture may create an osmotic pressure in one portion sufficient to burst the separating membrane thereby causing mixing of the oscillation reactants. Once initiated, the reaction oscillates according to the defined characteristics of the system.

BRIEF DESCRIPTION OF THE DRAWINGS

FIG. 9 shows the results from the flux study of benzoate ion through 2 mil, 28% EVA film at 32° C.

DETAILED DESCRIPTION OF THE INVENTION

Figure 1A:
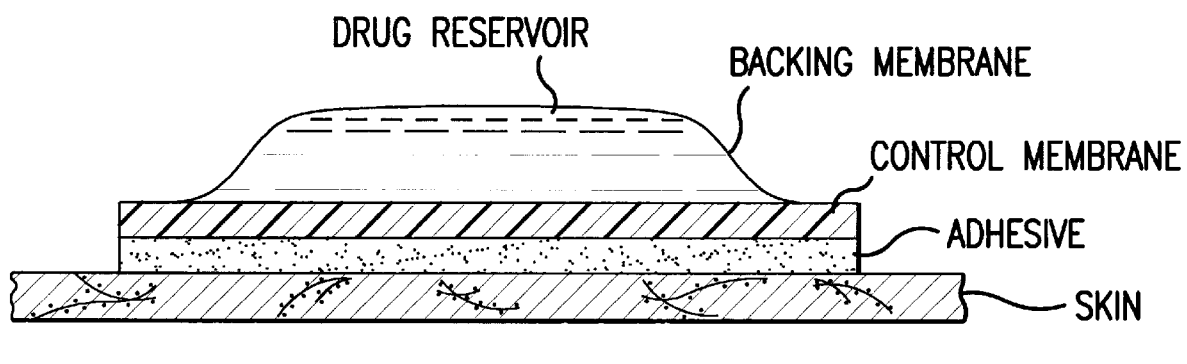
FIG. 1A–1D illustrates the development of strategy for temporal drug delivery systems.

The present invention is a method of using chemical oscillators, including pH and/or redox oscillators, to produce a temporal or periodic release of a drug or an active ingredient by preferably passive means across a membrane. To achieve oscillating drug diffusion, a strategy was formulated to oscillate the input in order to obtain an oscillating output profile. This may be accomplished in a variety of manners in a variety of delivery systems which are suitable for use in delivering pharmaceuticals (especially, antiasthmatics, anticancer drugs, anti-AIDS medications, anti-parkinsonian drugs, anti-anginals, adrenergics, Alzheimer's and stroke medications, anti-viral agents, antisense peptides, anti-ulcer medications, PMS therapeutics, analgesics, endocrine/reproductive therapeutics, birth control medicaments, general hormone replacement therapeutics, including steroids and steroid derivatives, stroke medications, antibiotics, immunizations, addiction treatments, anxiolytics, antisensitization drugs, antiirritants, anti-inflammatories such as NSAIDS, antiarrhythmics, etc.), contrast media for photo-imaging (imaging agents), cosmetics (such as perfumes and fragrances, moisturizers, deodorants, conditioners, etc.), agricultural active agents (such as pheromones, insecticides, herbicides, or growth regulators), etc.

Pharmaceutically active agents particularly include luteinizing hormone releasing hormone (LHRH), parathyroid hormone (PTH), PTH fragments, PTH analogs, somatistatin, somatistatin analogs, melatonin, insulin, insulin-like growth factor (IGF-1), nicotine, nitrosoureas, steroids, steroid derivatives, gastric acid inhibitors, nitrates, beta-blockers, progesterone, aldactone, seratonin, melatonin, sleep-inducing peptides, dehydroepiandosterone (DHEA), non-steroidal anti-inflammatory drugs (NSAIDS), bone morphogenic proteins (BMP), and adrenocorticotropic hormone (ACTH).

The balance of this disclosure will be tailored to pharmaceutical products, but the invention disclosed and exemplified can be applied equally well to any other area where temporal control or periodic release of an agent is desired, including veterinary products.

For purposes of this invention, "passive delivery" means that once the oscillation is begun, no other source of energy (outside of the system) is needed to drive the oscillation reaction and the delivery of active agent follows passive diffusion principles (i.e. flux of a species follows its chemical potential gradient from high to low) depending on the species of the active agent, the pH of the system and/or the oscillation reaction responsive characteristics of the delivery device per se.

In general, the present invention control of an active agent can be seen with specific reference to pH and/or redox oscillating reactions. However, any other oscillating species in an oscillating reaction can advantageously be employed in a similar fashion. For purposes of simplicity, the invention will be described with specific reference to pH and/or redox oscillating reactions.

With reference to oscillating systems in pharmaceutical contexts, the environment of the active agent to be delivered can have its state, i.e. pH, altered between a value where the active agent shifts between species which more readily and less readily permeates or diffuses through a delivery device barrier (and/or, in the case of a transdermal, the skin); a membrane barrier through which the active agent must pass or a matrix from which the active agent must be released can have its permeability altered in response to oscillation changes; a barrier separating a flux enhancer from the active agent can be modulated to regulate the amount of flux enhancer delivered to the active agent and as a result modulate the flux enhancer dependent active agent delivery; a polymer can be modulated to shift between a more viscous and less viscous form (i.e. poly-γ-glutamate as in Creacenzi et al., Polymer Preprints, August 1994, 407–408) or a more solubilized and less solubilized form or a more swollen and a less swollen form (i.e. poly(meth)acrylic acid as in Kou et al., Pharmaceutical Research 5, #9, 1988, 592–597), thereby altering the amount of water available to the active agent or another membrane which either needs to be or needs not to be hydrated in order to have proper active agent delivery, etc.

Where a lipophilic membrane is involved, either as part of the delivery device or as a membrane of the patient through which the active agent must pass (and is not changed by the environment through which it passes after leaving the device and before arriving at the lipophilic membrane), the combination of an active agent, preferably a drug, with a chemical oscillating reaction, may render the active agent charged or uncharged relative to its own pKa value. Since only the uncharged form of a drug can permeate across lipophilic membranes, a periodic delivery profile may be obtained by oscillating the state, i.e. pH, of the drug solution. The same type of end result can be achieved by oscillating the permeability of a membrane to either the active agent per se or to a flux enhancer needed for active agent delivery.

Some or all of the above components may also be adapted for use in delivery devices of other types, such as capsules, tablets, etc. These are especially suited for use with active agents which are rapidly cleared from the system and therefore need to be administered repeatedly over the course of a day. Any disease state which will be better treated by intermittent low dosing of the active agent (such as chemotherapeutic agents) can also benefit from the present invention. A suitable membrane for use which is permeable to uncharged species of active agents, but not (or at least substantially less) permeable to charged species of the active agent and not (substantially not) permeable to oscillation reaction components is ethylene/vinyl acetate (EVA) copolymer. Other suitable membranes will be apparent to those of ordinary skill in the art. In another variant, the active agent is not contained in the same compartment with the oscillation reaction components, but in a separate compartment. Both compartments are contained within another membrane which is permeable (or more permeable) to one form of the active agent. The oscillation changes of the reaction communicates through the EVA membrane to the active agent containing compartment. In response to the changing state, the active agent shifts between states in which it has greater and lesser ability to diffuse out of its compartment and into the outer environment. Other variations adapted from the embodiments described concerning the transdermal systems will be apparent to those of ordinary skill.

Strategy for Temporal Drug Delivery

The key parameter for system design is the ratio of the characteristic time for permeation to the characteristic time of the oscillating driving force. This ratio must be small (less than one) to produce a temporally controlled delivery profile. As an example, a periodic drug release profile can be obtained by ensuring that the period of oscillation in the drug input through the use of a pH chemical oscillator is longer than the permeation of the drug across all diffusional barriers. The following analysis illustrates how this key parameter controls the delivery of a drug across a membrane. Consider an ideal situation where a drug with a known pKa is in an infinite reservoir, in which the pH of the solution is periodically changed by a pH chemical oscillator. The instantaneous concentration of the uncharged form of the drug [C(t)], which can permeate across a hydrophobic membrane, is given by:

$$C(t) = C_{max} \sin(\omega t)$$

where $C_{max}$ is the maximum concentration, t is time, and $\omega$ is the frequency (or $2\pi/\omega$ is the period of oscillation). The frequency, $\omega$, is controlled by the kinetics of the pH oscillation, and hence by the selection of the chemical oscillator. The flux of the drug across the membrane, expressed in a dimensionless form, is then given by:

$$-\underbrace{\frac{lj(t, x=0)}{2KDC_{max}}}_{\text{dimensionless flux}} = \sum_{n=1}^{\infty} (-1)^{n+1} n^2 \left\{ \underbrace{\frac{1}{(n^4 + \lambda^2 \omega^2)^{1/2}} \sin\left[\omega t - \tan^{-1}\left(\frac{\lambda \omega}{n^2}\right)\right]}_{\text{forced oscillation}} + \underbrace{\frac{\lambda \omega}{(n^4 + \lambda^2 \omega^2)} e^{-n^2 t/\lambda}}_{\text{diffusion}} \right\}$$

where l, K, D and $\lambda$ (=$l^2/\pi^2 D$) are the thickness of the membrane, the partition coefficient, the diffusivity and the characteristic time of permeation. The permeation characteristic time, which is theoretically proportional to the time lag, is governed by the diffusivity and the thickness of the membrane, shown in FIGS. 1A–1D. The first term in the right-hand-side of the above equation describes the contribution to the flux by the imposed periodic change of the driving force, whereas the second term is the dampening of the drug transport by the membrane. Consequently, if the conditions are set up such that the second term dominates ($\lambda \omega \gg 1$), then the output flux would always be controlled by the membrane to a constant value that reflects the mean driving force for diffusion. However, if the conditions are set up such that the first term dominates ($\lambda \omega \ll 1$), then the flux of the drug across the membrane would oscillate at the same frequency as the drug in the donor changes from a charged to an uncharged state. Defining this set of conditions, in which $\lambda \omega \leq 1$, is the underlying principle for the development of the temporally controlled delivery system.

Proposed Mechanisms of Chemical Oscillators

Numerous chemical oscillation reaction, including pH and/or redox reactions, are known in the art. Non-pH oscillating reactions that can be used in the invention include, but are not limited to, $Ce^{+3}$, $Mn^{+2}$, $Fe^{+2}$, $Li^+$, and $Ru^{+2}$ complexes in the BZ reaction, $S^{+2}$—$O_2$-methylene blue system, the Briggs-Rauscher (BR) reaction, the Landolt reaction, and horseradish peroxidase reaction (Geest, et al., J. Phys. Chem. 96:5678–5680 (1992) and *Chemical Chaos*, Scott, Clarendon Press: Oxford p. 423 (1991)) as well as those shown in Table 7.1 in Oscillations and Traveling Waves in Chemical Systems; Field and Burger, Eds; Wiley-Interscience, New York (1983), p.230. Further non-pH oscillating reactions include peroxide-urea/phthalic anhydride system and peroxinitrite system.

Two of the earliest recognized chemical oscillators are the Belousov-Zhabotinskii (BZ) reaction and the Landoldt or "iodine clock reaction". (Nicholos et al., Chemical Oscillators, Chemical Reviews, 1973, Vol. 73, No. 4, p 365–384.) Neither of these are pH driven oscillating systems.

The BZ reaction is one of the most extensively studied non-linear reactions known today. Under appropriate conditions, organic materials are oxidized by bromine or other halide with the aid of a metal-ion catalyst which leads to self-sustained oscillations in the concentrations of the reaction intermediates. These oscillations can be seen visually by the addition of the reagent ferroin (see Field, Chem. Ed., Vol. 49, No. 5, 1972, p. 108). The accepted Field, Koros and Noyes (FKN) mechanism was presented in 1972 by Field, Koros and Noyes (Tyson, John; in Oscillations and Traveling Waves in Chemical Systems; Field and Burger Eds.; Wiley-Interscience, New York (1983), p.94). In a more simplified form, it is known as the Oregonator (p. 108 of this same reference), shown below:

A+YHX

X+YHP

B+XH2X+Z

2XHQ

ZHfY

In this model, A and B are reactants, P and Q are products, X, Y and Z are the concentrations of the intermediates (bromous acid, bromide ion, and Ce(IV), the metal-ion catalyst), and f is the stoichiometric factor, respectively (Epstein, I. R.; Orban, M. in Oscillations and Traveling Waves in Chemical Systems; Field, R. J., Burger. M., Eds.; Wiley-Interscience: New York, (1983)). The usual practice for the study of oscillating systems has been to use closed (batch) reactors or an open system (continuous flow stirred tank reactor (CSTR)). The recent description of using a "semibatch reactor" as an additional tool, is an appealing and simple intermediate method to study pH oscillating systems (see Rabai and Epstein, J.A.C.S. 114, above).

In the BZ reaction, which is the catalytic halogenation (preferably bromination) and oxidation of an organic substrate, the organic substrate fluctuates between two species, the halogenated and the unhalogenated compound. Differences between these two species in any of the parameters needed for effective delivery can be exploited to obtain the desired delivery control. Typical substrates for use in this reaction include, but are not limited to, citric acid, malonic acid, bromomalonic acid, malic acid, gallic acid, pyruvic acid, oxalic acid, 2,3-pentanedione, quercetin, morin, acetoacetic acid methyl ester, 4-chloroacetoacetic acid ethyl ester, acetonedicarboxylic acid diethyl ester, N-methylacetoacetamide, acetylacetone-chromium complex, 3,4,5-trimethoxybenzaldehyde, 2,4,5-trimethoxybenzaldehyde, and (in a water-acetonitrile solution) a mixture of veratric acid and veratraldehyde. Polymers having these materials incorporated therein (typically as pendent groups) in at least 40% of the repeating units of such polymer can also be used in the polymeric embodiments described further below.

Similar to the BZ reaction is the classical Briggs-Rauscher (BR) reaction. See Vanad and Alfimov, J.Phys. Chem. 97:1878–1883 and 1884–1890 (1993). This reaction is the $Mn^{2+}$-catalyzed oxidation of malonic acid by iodate and hydrogen peroxide in sulfuric or perchloric acid and is accompanied by oscillations in the concentrations of iodine, iodide, and triiodide, as well as other reaction characteristics.

The Briggs-Rauscher reaction is a light-induced oscillation in that the oscillation between states may be induced by light. Other light-induced oscillations are known in the art, including those described in Yui, et al. J. Controlled Release, 26:141–145 (1993) and Yoneyama, et al. J.Am. Chem. Soc. 116:7294–7298 (1994).

Figure 2:
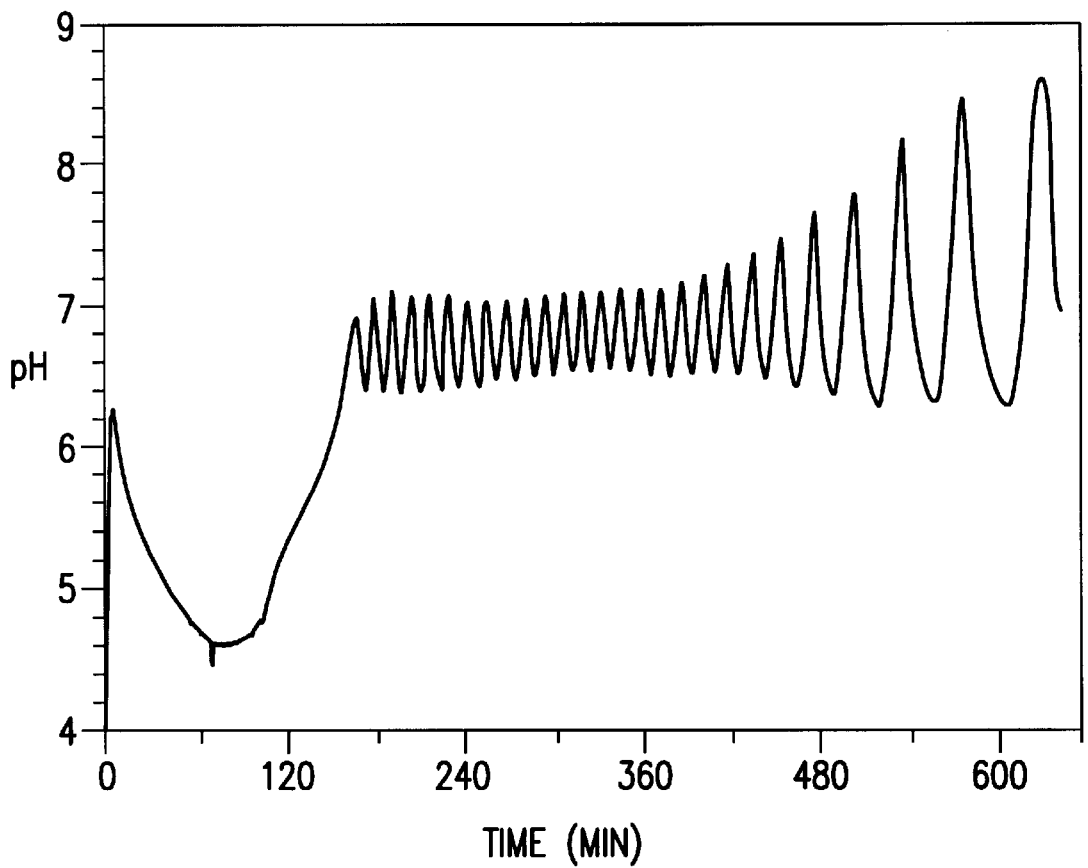
FIG. 2 shows pH oscillations observed in the semibatch Hydrogen peroxide-Thiosulfate reaction under the conditions where Solution A (0.05 M $Na_2S_2O_3$ containing 0.07 M NaOH) is introduced into 300 mL of Solution B (0.10 M $H_2O_2$ and $8.8 \times 10^{-6}$ M $CuSO_4$) at 0.225 mL/min.

Initial experimentation of pH oscillators started with the Cu(II) catalyzed hydrogen peroxide oxidation of thiosulfate in order to determine experimental parameters. Using the concentrations reported by Rabai and Epstein (J.A.C.S. 114, above), we obtained the same type of pH oscillations, with the exception of a longer period length due to a differing residence time of the reactor (FIG. 2). Even though a detailed mechanism has not been suggested for this system, the oscillations can be explained by the fact that the oxidation of thiosulfate by hydrogen peroxide can occur through two reaction routes:

$$2S_2O_3^{2-}+H_2O_2HS_4O_6^{2-}+2OH^- \qquad (1)$$

$$S_2O_3^{2-}+4H_2O_2H2SO_4^{2-}+2H^++3H_2O \qquad (2)$$

This competition between the production of OH⁻ and of H⁺ has generally been assumed to be the driving force responsible for the pH oscillations, at least under CSTR conditions (Orban and Epstein, J.A.C.S. 109: 101, 1987)). When hydrogen peroxide is in excess, as it is in the semibatch reactor, the hydrogen ion producing reaction (eq. 2) predominates. As the peroxide concentration falls with respect to thiosulfate, the hydroxy producing reaction begins to take over and pH climbs. Once the peroxide concentration drops significantly relative to thiosulfate, the hydrogen ion producing reaction again kicks in and the pH again falls. The addition of hydroxide is essential in order to make reaction (1) competitive (Rabai and Epstein, J.A.C.S. 114, above).

The mixed Landoldt reaction (iodate-thiosulfate-sulfite) oscillates the pH between 6.5 and 4.0. With this oscillating system there is a characteristic "spike" where the pH minimum is just above 4.0. If the pH falls below 4.0 for any length of time, the iodate-iodide (Dushman) reaction predominates and the solution turns brown in color. The model mechanism for this reaction is as follows:

A+B⇌Y

A+B+X⇌P1

Figure 3A:
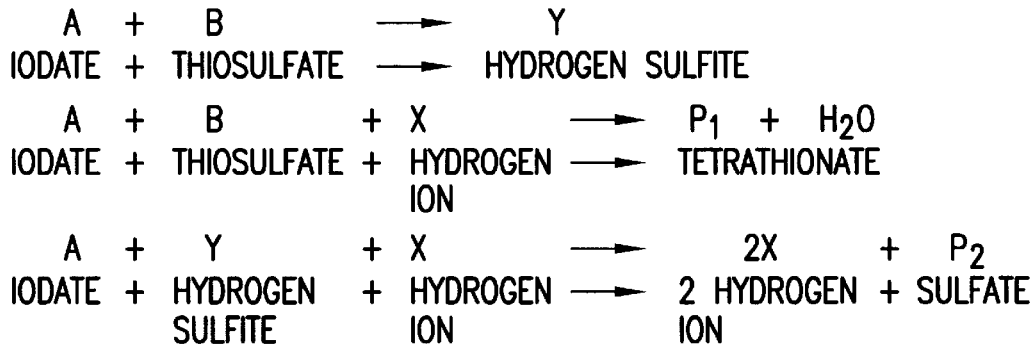
FIG. 3 illustrates the model mechanism and schematic diagram for the Iodate-Sulfate-Thiosulfate pH oscillator.
Figure 3B:
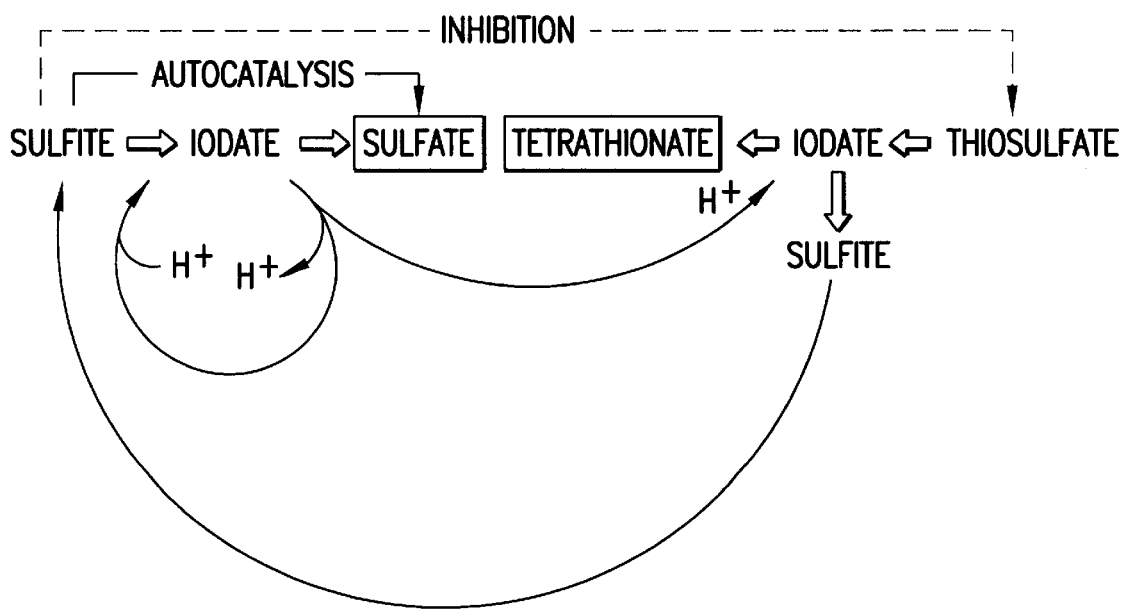

A+Y+X⇌H2X+P2 where in this skeleton model, A corresponds to (but does not stand for) iodate, B to thiosulfate, Y to hydrogen sulfite, X to hydrogen ion, P1 to tetrathionate and P2 to sulfate. The basis for the oscillatory behavior is the alternation of the autocatalysis of sulfite and the consumption of hydrogen ion and the formation of sulfite (Rabai and Beck, above) [see FIG. 3).

The Mixed Landoldt oscillator, which is the iodate oxidation of sulfite with an additional reductant in acid solution, is a well known pH oscillating system. When thiosulfate is chosen as the additional reductant, pH regulated oscillations can occur between the values of 6.5 and 4.0. This system has been extensively studied by Rabai and Beck for batch and CSTR conditions and Rabai and Epstein for semibatch conditions (Rabai, G. and Epstein, I. R. J. Am. Chem. Soc. 114 1529 (1992); Rabai, G., and Beck, M. T. J. Phys. Chem. 92 4831–4835 (1988); and Rabai, G. and Beck, M. T. J. Phys. Chem. 92 2804–2807 (1988)). In oscillating chemical reactions, the concentrations of catalyst or intermediate species, such as metal ions, oscillate with time. They are driven by a decrease in free energy of the overall chemical reaction occurring far from thermodynamic equilibrium (see Luo and Epstein above).

Other pH oscillating reactions include, but are not limited to:

the iodate-sulfite-thiourea system;

the iodate-sulfite-thiosulfate system;

the iodate-sulfite-ferrocyanide system;

the bromate-sulfite-ferrocyanide system;

the iodate-hydroxylamine system;

the periodate-hydroxylamine system;

the phenol-bromite-hydroxylamine system (pH 3–7) Orban, J. Phys. Chem. 1994, 98, 2930–2935;

the periodate-thiosulfite system;

the hydrogen peroxide-ferrocyanide system;

the hydrogen peroxide-thiosulfate-copper(II) system;

the hydrogen peroxide-sulfite-ferrocyanide system (pH 4.5–7) Rabai et al., J. Phys. Chem., 1994, 98, 2592–2594;

the chlorite-thiocyanate system (pH 1–4) Chinake et al., J. Phys. Chem. 1994, 98, 2908–2916;

the chlorite-iodide-malonic acid system;

the chlorite-thiourea system (pH 2.5–4.5) Epstein et al., J. Phys. Chem. 1992, 96, 5852–5856; and bromide-hydroxylamine-phenol (Orban and Epstein, J.Phys. Chem. 98:2930–2935 (1994)).

The Mixed Landoldt oscillator, which is the iodate oxidation of sulfite with an additional reductant in acid solution, is a well known pH oscillating system. When thiosulfate is chosen as the additional reductant, pH regulated oscillations can occur between the values of 6.5 and 4.0. This system has been extensively studied by Rabai and Beck for batch and Continuously Stirred Tank Reactor conditions and Rabai and Epstein for semibatch conditions (Rabai, G. and Epstein, I. R., J. Am. Chem. Soc. 114 1529 (1992); Rabai, G., and Beck, M. T. J. Phys. Chem. 92 4831–4835 (1988); and Rabai, G. and Beck, M. T. J. Phys. Chem. 92 2804–2807 (1988)). In oscillating chemical reactions, the concentrations of catalyst or intermediate species, such as metal ions, oscillate with time. They are driven by a decrease in free energy of the overall chemical reaction occurring far from thermodynamic equilibrium (see Luo and Epstein above).

Any of these can be used in the practice of the invention, depending upon the use to which the product will ultimately be put. Generally, where one halogen is used, it may be substituted with the corresponding species of another halogen, for example bromate replacing iodate or bromite replacing chlorite.

Preferably, for pharmaceutical uses, the pH oscillators of the iodate-hydroxylamine system, the iodate-sulfite-thiosulfate system, the bromate-sulfite-ferrocyanide system, and the hydrogen peroxide-thiosulfate-copper(II) system are used.

Each of the pH oscillators has a defined range of pH through which it will oscillate, making the choice of oscillator dependent upon the characteristics of the other materials chosen in the construction of the delivery device. Some of the pH oscillation reaction pH ranges are shown below in Table 1. Others will be readily determined by those of ordinary skill in the art using known techniques.

TABLE I pH REGULATED OSCILLATORS

| SYSTEM | pH RANGE |
| --- | --- |
| 1) IODATE-SULFITE-THIOUREA | 7.5–3.5 |
| 2) IODATE-SULFITE-THIOSULFATE | 6.5–4.1 |
| 3) IODATE-SULFITE-FERROCYANIDE | 2.5–8.0 |
| 4) IODATE-HYDROXYLAMINE | 2.8–5.5 |
| 5) PERIODATE-HYDROXYLAMINE | |
| 6) PERIODATE-THIOSULFATE | 4.0–6.0 |
| 7) HYDROGEN PEROXIDE-FERROCYANIDE | 5.0–7.0 |
| 8) HYDROGEN PEROXIDE-THIOSULFATE-COPPER(II) | 6.0–8.0 |
| 9) HYDROGEN PEROXIDE-BISULFITE-THIOSULFATE | |
| 10) PEROXODISULFATE-THIOSULFATE-COPPER(II) | 2.3–3.0 |
| 11) BROMITE-IODIDE | |
| 12) BROMATE-SULFITE-FERROCYANIDE | 4.5–6.5 |
| 13) BROMATE-SULFITE-THIOSULFATE | 4.5–6.5 |
| 14) MANGANESE(II)-PERIODATE | 3.5–4.5 | pH     2.0   3.0   4.0   5.0   6.0   7.0   8.0

SYSTEM

Peroxodisulfate        |———|

Permanganate          |————|

Iodate                |———|

Peroxide              |————|

Bromite-iodide         |————|

Iodate-sulfite-              |————————| ferrocyanide (theoretical)

The delivery devices into which the oscillating reactions can be incorporated include tablets, capsules, implants, impregnated bandages, and transdermal delivery devices. The delivery devices have at least one barrier layer, which is a membrane coat through which the active agent must pass or a matrix from which the active agent must be released. In the simplest systems, this membrane or matrix is permeable to one species of the active agent, but not another species of the active agent, and the active agent changes between these species in response to the pH changes in the oscillating reaction. Such a transdermal system is demonstrated by a cavity formed by an ethylene/vinyl acetate membrane to which is laminated a silicone based pressure-sensitive adhesive, heat sealed to a polyester impermeable backing. Inside the cavity is a reservoir containing the active agent and pH oscillator reactants. In this embodiment, since there is no separation of the oscillator reactants, the system is active upon assembly. This is suitable for a so-called "fillable" transdermal system in which the one or more of the oscillator reactants are left out of the system until it is ready for use. At that time, the final reactants are added and the system is active. In a slightly more complex system, multiple compartments are present with at least one oscillation reaction reactant separated from the rest of the reactants. The separation barrier between these compartments is burstable or removable by the user, thereby activating the oscillation reaction, just before applying the transdermal. These separation barriers include, but are not limited to, poly(siloxanes), poly(carboxylic acid), poly(sulfonic acid), poly(acrylamide), poly(hydroxylamine), poly(phosphonic acids), poly(amino acids), poly(vinyl alcohol), and poly(N-vinyl-2-pyrrolidone), poly(meth)acrylates, cellulosics, alginates, chitosan, starches, hyaluronic acid, collagen, iodine-doped polymers, polyesters, polyamides, polyurethanes, ion exchange resins, polyelectrolytes, poly(hydroxamic acids), and poly(ethylene oxides).

Alternatively, if the oscillation reaction is either initiated by light one of the reactants is converted to an active form by light, then all of the reactants can be combined in a single compartment provided the initiating radiation is excluded, i.e. by a user-removable, light impermeable membrane, until one desires to initiate the oscillation reaction. Examples of actinic radiation initiated oscillation reactions include, but are not limited to those disclosed in: DD 146864 (published Mar. 4, 1981) (photosensitive Fe(III) compound-bromate-organic acid-dipyridyl complex former); Mori et al., J. Phys. Chem. 1994, 98, 12968–12972 (ferrocyanate-peroxide-sulfuric acid); Rabai et al., J. Phys. Chem. 1994, 98, 10550–10553 (chlorite-cloride-iodomalonic acid); and Vanag et al., J. Phys. Chem. 1994, 98, 8392–8395 and Mori, J. Phys. Chem. 1992, 96, 9083–9087 (peroxide-sulfite-ferrocyanide).

The various dosage forms which are suitable for use in the present invention include tablets, capsules, depot formulations for insertion into the body, topical preparations, transdermals, impregnated bandages, infusions, etc. In each case, the delivery device must either have a means for preventing the initiation of the oscillation reaction until it is desired that the reaction begin, or the device is capable of having at least one component added by either the user or the administrator of the device so as to activate the oscillation reaction. Beyond these criteria and that the device components be compatible with the chosen oscillation reaction, any standard delivery device materials may be used.

Transdermals include all the various types known in the art including, reservoir, matrix, gel including hydrogel, and non-woven. A typical transdermal device is shown in FIG. 1A. It has an impermeable backing layer or laminate which is sealed to a control membrane, and together define a reservoir area. On the control membrane, distal to the backing layer, is an adhesive. FIG. 1A shows the device as applied to the skin of the user. Prior to applying the device to the skin, the typical transdermal device has a removable layer or laminate in place of the skin in FIG. 1A. The reservoir may contain the drug to be delivered, or the drug may be within either the control membrane or the adhesive. The oscillation reaction reactants are placed in the reservoir area by any suitable means (such as a resealable entry port for inserting the reactants).

Once the oscillation reaction reactants are all present, the oscillation reaction starts. The oscillations obtained can modulate the drug itself or a needed flux enhancer (such as dimethylsulfoxide, azone, limonene, etc.) to effect delivery; modulate the membrane to open and close the control membrane "gate" to either the drug or to a needed flux enhancer (i.e. pore size modulation and/or chemical compatibility of the membrane for the species which must diffuse therethrough—see Islam et al., Journal of Applied Polymer Science, vol. 45, 1485–1490 (1992)—polyethylene; Israels et al., Macromolecules 1994, 27, 6679–6682; Lee et al., J. of Controlled Release, 6, (1987) 3–13); modulate the viscosity of the reservoir or adhesive, including use of a viscosity enhancer, (such as PAMPS, polyethyleneoxides, poly(meth)acrylic acid, polyvinyl alcohol, polyvinylpyrrolidone, poly-γ-glutamic acid etc.) to enhance or impede drug or flux enhancer travel therethrough; or alter the available solvent (such as polyacrylamide gels, polyvinyl alcohol gels, PAMPS gels, etc.) to modulate the concentration of drug and/or enhancer.

Viscosity enhancers include, but are not limited to, poly(meth)acrylates, cellulosics, alginates, chitosan, starches, hyaluronic acid, collagen, poly(ethylene oxides), poly (sulfonic acid), poly(acylamide), poly(carboxylic acid), poly (hydroxylamine), poly(phosphonic acids), poly(amino acids), poly(vinyl alcohol), iodine-doped polymers, polyesters, polyamides, polyurethanes, cyclodextrins, non-ionic surfactants, gelatin gels, lecithin-ogranogels, ion exchange resins, polyelectrolytes, poly(hydroxamic acids), poly(3-carboxymethylpyrrole), borohydride exchange resins, oxidizing reagent polymers, and poly(N-vinyl-2-pyrrollidine).

Figure 10A:
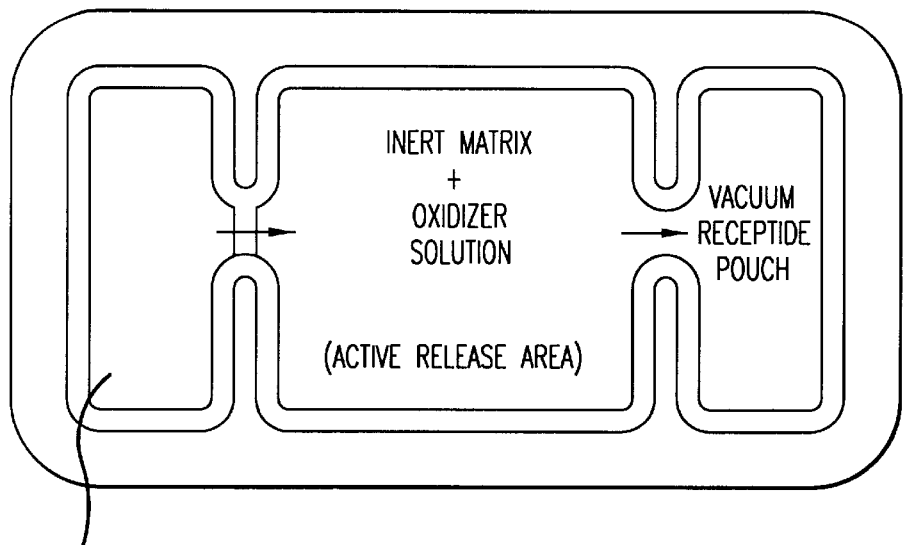
FIG. 10 illustrates an example of a user activated transdermal system for the temporal release of active compounds. Although the compartments are shown as being side-by-side, they may alternatively be layered on top of each other.
Figure 10B:
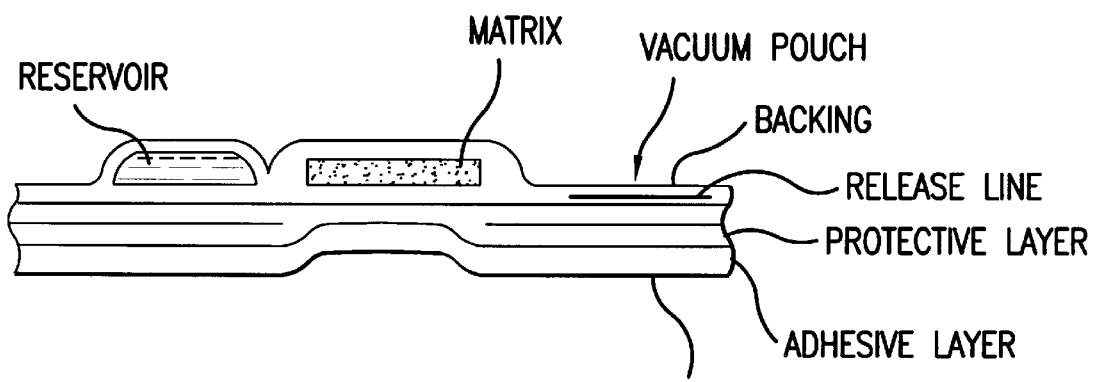

A more typical transdermal device is shown in FIG. 10. This device has an impermeable backing and a release liner or membrane or laminate. These two layers are sealed together so as to define between them at least three separate compartments. In one compartment is the bulk of oscillation reaction components. In the case shown, this is PAMPS, $Na_2SO_3$, $Na_2S_2O_3$, and the drug desired to be delivered. This is adjacent to a second compartment having a matrix and the oxidizer solution contained therein. In the specific example in FIG. 10, the oxidizer would be $IO_3$. This compartment corresponds to the active agent release area. Distal to the first compartment, but adjacent to the second compartment, is a third compartment which is a vacuum receptacle compartment. To prevent drug migration inappropriately, compartments 1 and 3 have an overlayer on the release layer (distal to the compartments themselves) which is impermeable to the drug. Further distal to the compartments and covering the overlayers as well as the remainder of the release layer is an appropriate transdermal adhesive. The final covering on the adhesive is a removable protective layer which is removed by the user or an administrator of the device just prior to its application to the body to be treated.

In this embodiment, compartments 1 and 2 are separated by a burstable impermeable membrane. This burstable membrane is broken by the action of the user or administrator just before or just after (preferably before) removal of the release layer.

The instant invention may also be in the form of a bandage. Such bandage would be constructed and operate in a manner similar to that of the transdermal, but would be of larger surface area.

The invention may further be in the form of a tablet. A tablet can be constructed having the oscillation reaction components in a core along with a compatible active agent which exists in a diffusible and non-diffusible form. The core is surrounded by a membrane which is permeable to the active agent diffusible form. Upon reaching the stomach, the acid environment diffuses into the core and initiates the oscillation reaction which then results in local changes which override the influences from the gastrointestinal environment allowing for periodic delivery of the active agent.

The instant invention may even further be in the form of a capsule. For such form to be functional, the capsule should contain at least two chambers and a barrier to separate the initial reactants from the oxidizer or to separate out some of the initial reactants such that the oscillation reaction would not begin prior to ingestion of the capsule. Initial reactants, as used herein, is intended to designate those reactants necessary to start the oscillation reaction. Upon ingestion, the oscillation reaction would be initialized by the reactants diffusing through the barrier and the reaction would proceed in the same general manner as in other dosage forms.

A specific embodiment of such capsule form would be a capsule separated into two chambers; the first containing the initial reactants, such as in the form of an OROS®-type capsule, and the second containing an oxidizer and the active agent. The first chamber would be formed of a semi-permeable membrane or material such that water/gastric fluid could diffuse into the chamber, but the reactants contained in the chamber could not diffuse out. The second chamber would be formed of a semi-permeable membrane or material such that the active agent could diffuse out of the chamber, but water/gastric fluid could not diffuse in. The two chambers would be separated by a barrier formed of a membrane which would allow the initial reactants to diffuse from the second chamber into the first. Upon ingestion, water/gastric fluid would diffuse into the first chamber, allowing the initial reactants to diffuse into the second chamber. This would initialize the oscillation reaction and the flux of active agent out of the capsule in a manner similar to that of the other dosage forms.

Another embodiment of such capsule would have the addition of a third chamber formed of a impermeable material. This third chamber would be separated from the second chamber by a barrier diffusible to the reaction products. As the reaction products built up, they would diffuse into the third chamber. In this embodiment, the oscillation reaction could proceed for a longer time period as the reaction would not be damped by the reaction products.

Capsules could also be prepared with microencapsulated versions of the above described tablets.

The initial invention may still further be in the form of an implant, such as a passive or active infusion pump. The construction of such device is known in the art. In this embodiment, the active agent and the initial reactants would be imbedded in a central core of polymer. The same polymers may be used as in the transdermal devices, i.e. PAMPS. This central core would be surrounded by an outer layer composed of a non-reactive, non-toxic material, such as silicone. Upon activation by diffusion inward of bodily fluids, the active agent changes between a diffusible and a non-diffusible state and diffuses out of the pump and into the body in the same general manner as in the transdermal.

The above infusion pump may also be percutaneous in which case activation may be by the user/administrator adding water to hydrate the initial reactants. Alternatively, the user/administrator could add the initial reactants prior to use such that the device is reusable.

In an alternative infusion pump, the pump would further consist of a barrier between the central core and the outer layer and/or between the outer layer and the body. This barrier would react to the chemical oscillation such that it alternates between a permeable and a non-permeable state with respect to the active agent. Thus, in one oscillation state, the barrier would allow and in the other oscillation state, the barrier would substantially bar active agent diffusion out of the pump.

EXAMPLES

The following nonlimiting examples further describe the present invention.

Compounds that were used: All chemicals were of reagent grade and used without further purification. Sodium iodate, sulfuric acid (volumetric standards 0.5 N and 0.1 N), poly (ethylene oxide)—MW 4,000,000 and 900,000 and poly(2-acrylamido-2-methyl-1-propane sulfonic acid) 10 wt. % in water (PAMPS), were obtained from Aldrich Chemical Co., Milwaukee, Wis. Sodium thiosulfate, sodium sulfite, sodium iodate, (−)-nicotine (free base), cupric sulfate, malonic acid, citric acid, ceric ammonium nitrate and hydrogen peroxide (30% w/w solution) were obtained from Sigma chemical Co., St. Louis, Mo. Poly(acrylic acid)—MW 450,000 and 250,000 was obtained from Polysciences Inc., Warrington, Pa. Potassium bromate, sulfuric acid (18 M), pH buffer standards (4.00 and 7.00) and 1, 10 phenanthroline ferrous sulfate complex (Ferroin 0.025 M solution) were obtained from Fisher Scientific, Pittsburgh, Pa.

pH oscillator experiments were carried out in a simple semibatch reactor or a custom made super cell diffusion cell apparatus obtained from Crown Bio-Science. The reactor, a 500 mL, 3 neck, round bottom flask, was fed by a Rainin Rabbit peristaltic pump using an Elkay pump tube (i.d. 1.14 mm). The reactor was stirred continuously with a magnetic stirrer. The pH of the reactor solution was monitored using a ROSS combination pH electrode connected to an Orion 520A pH meter. For standardization, potassium hydrogen phthalate buffers (pH 4.0 and 7.0) were used. Data acquisition was accomplished using an Apple Macintosh computer with Kaleidagraph software to produce the pH plots. Additional PC data acquisition software, HT BASIC, was used and the plots were produced using PS PLOT plotting program.

Example 1 pH Oscillations in a Semibatch Reactor

Cu(II) catalyzed hydrogen peroxide oxidation of thiosulfate—The pH semibatch experiments followed the conditions described by Rabai and Epstein (J.A.C.S 114, 1529 (1992)) for the semibatch reactor. The reactions were run using stock solutions of 0.10 M hydrogen peroxide ($H_2O_2$), 0.10 M sodium thiosulfate ($Na_2S_2O_3$), 0.14 M sodium hydroxide (NaOH) and $8.83 \times 10^{-6}$ M cupric sulfate ($CuSO_4$) which were prepared with deionized, distilled water. Briefly, 50.0 mL aliquots of the two stock solutions (sodium thiosulfate and sodium hydroxide) were combined into a 125 mL Erlenmeyer flask. This solution was then introduced, at 0.225 mL/min. using a peristaltic pump, into a 500 mL 3 neck round bottom flask containing 300 mL of 0.10 M hydrogen peroxide solution and 1.0 mL of the cupric sulfate solution. The reactor was used at room temperature and the solution was mixed by magnetic stirring.

Figure 4:
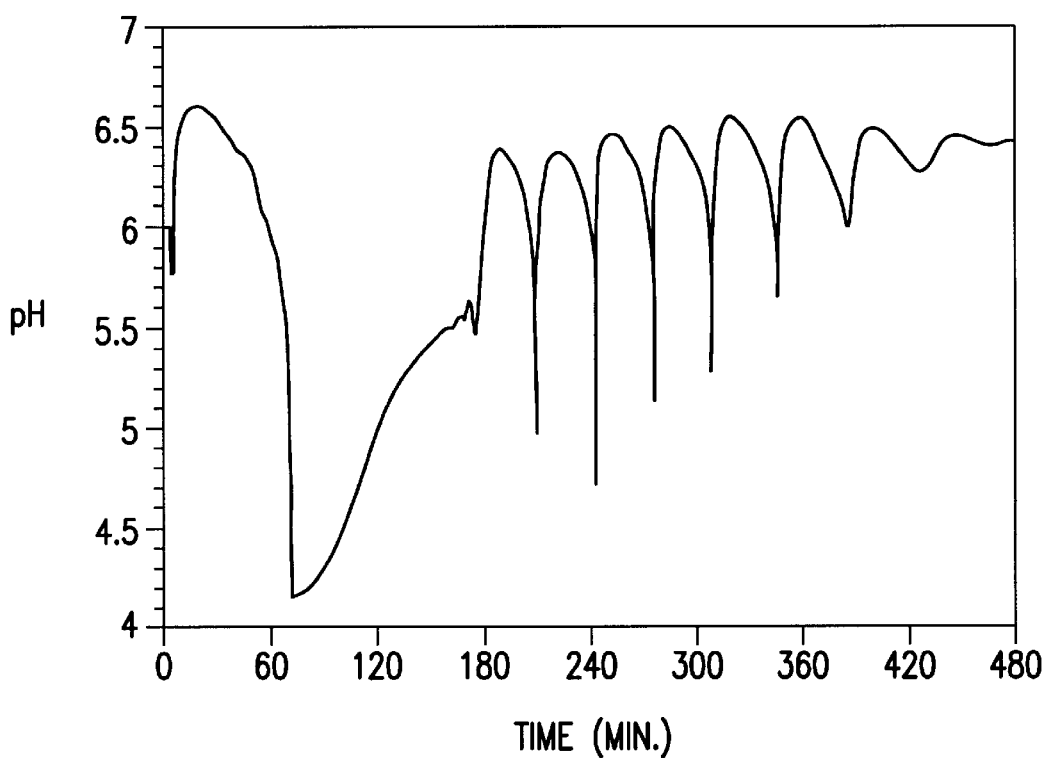
FIG. 4 shows the pH oscillations observed in the semibatch Iodate-Sulfite-Thiosulfate oscillator under the conditions where Solution A (0.02 M $Na_2S_2O_3$, 0.015 M $Na_2S_2)_3$ and 0.005 M $H_2SO_4$) is introduced into 300 mL of Solution B (0.05 M $NaIO_3$) at 0.225 mL/min.

Iodate-Sulfite-Thiosulfate—The reactions were run using stock solutions of 0.05 M sodium iodate ($NaIO_3$), 0.045 M sodium thiosulfate ($Na_2S_2O_3$) 0.06 M sodium sulfite ($Na_2SO_3$), 0.015 M sulfuric acid and several water soluble polymers which were prepared with deionized, distilled water. The solutions of $NaIO_3$, $Na_2S_2O_3$ and $Na_2SO_3$ were made fresh every week and protected from light during storage. The pH semibatch experiments followed the conditions described by Rabai and Epstein (J.A.C.S. 114, above) for the semibatch reactor with only minor changes. Briefly, 40.0 mL aliquots of the three stock solutions (sodium sulfite, sodium thiosulfate and sulfuric acid or water soluble polymer) were combined into a 125 mL Erlenmeyer flask. To avoid acidic decomposition of thiosulfate, the acid and sulfite solutions were measured first and then the thiosulfate solution was added. This solution was then introduced, at 0.225 mL/min. using a peristaltic pump, into a 500 mL 3 neck round bottom flask containing 300 mL of 0.05 M sodium iodate. Again, the reactor was used at room temperature and the solution was mixed by magnetic stirring. pH oscillations were obtained when sulfuric acid (0.005 M) was used as the acid component in the addition solution (FIG. 4). The pH was found to oscillate eight times between the values of 6.5 and 4.0 after an extended minimum induction period. Each cycle was approximately 30 minutes in length and towards the end of the experiment, the damped oscillations decreased in amplitude and increased in cycle time. This reaction was found to be consistently repeatable and not sensitive to fluctuations in room temperature. Additionally, the reactant concentrations were found to be interdependent. For example, when the thiosulfate concentration was reduced 7% or more, the pH decreases to below 4.0 during the induction period and the presence of elemental iodine appears. When thiosulfate concentration is increased 16% or more, the pH stays above 5.5 and the number of oscillations is reduced. The same effects were seen when the sulfuric acid concentrations were varied.

Example 2 pH Oscillations in a Semibatch Reactor with Polymer

Figure 5B:
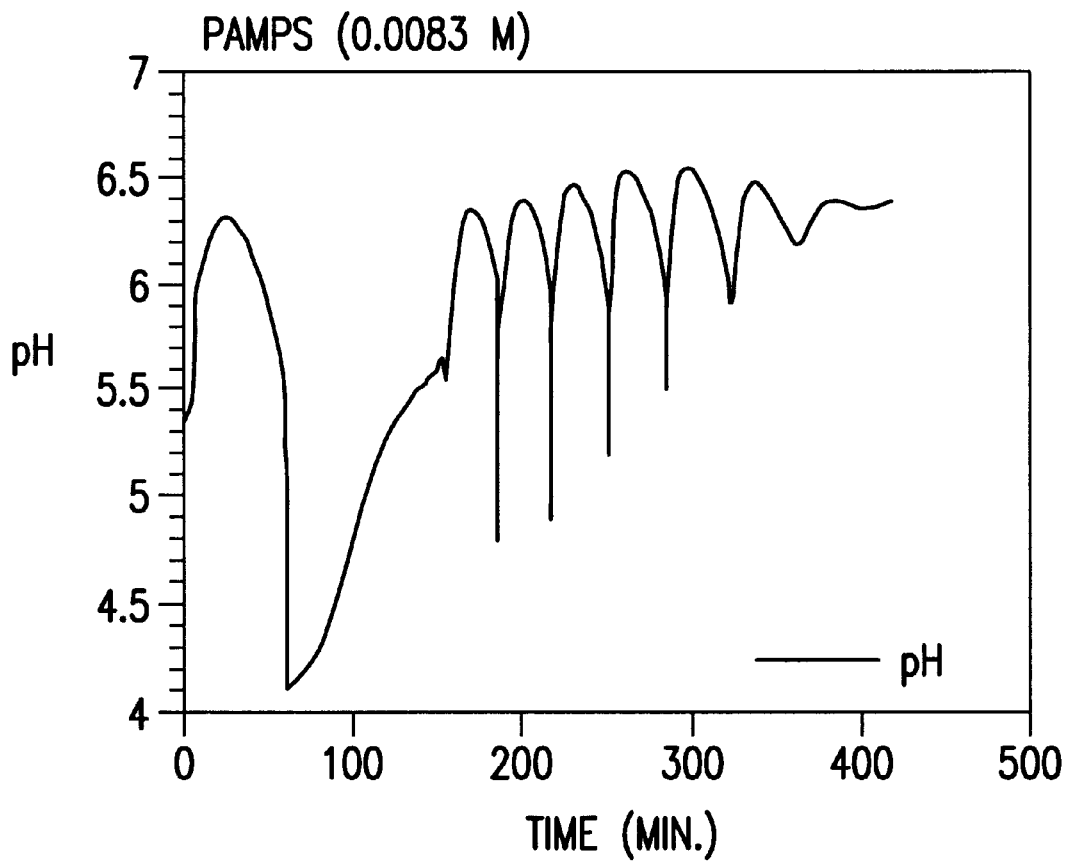
FIG. 5 compares the resultant pH oscillations when poly (2-acrylamido-2-methyl-1-propane sulfonic acid (PAMPS) (FIG. 5B) is directly substituted for sulfuric acid (FIG. 5A) in a semibatch reactor. In each case, solution A (0.02 M $Na_2SO_3$, 0.015 M $NaS_2O_3$ and either $H_2SO_4$ (FIG. 5A) or PAMPS (FIG. 5B)) is introduced at 0.225 mL/min using a peristaltic pump into 300 mL of Solution B (0.05 M $NaIO_3$) in a 500 mL, 3 neck, round bottom flask with magnetic stirring.
Figures 1, 5B:
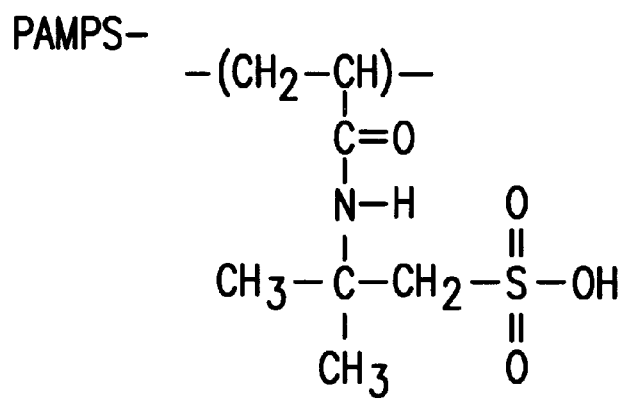
Figure 6A:
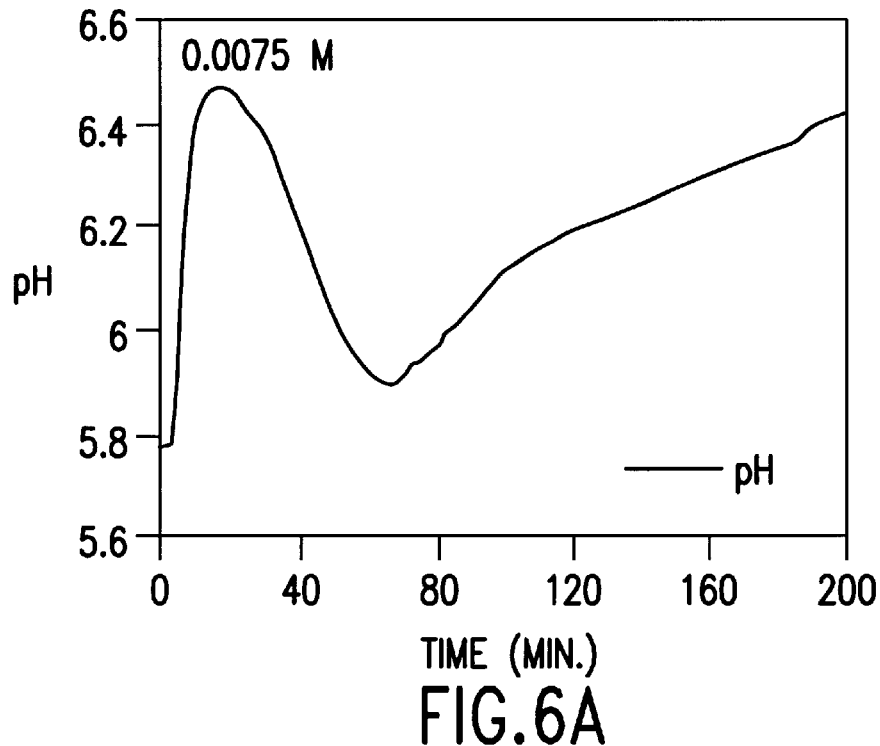
FIG. 6 shows the results of the Iodate-Sulfite-Thiosulfate-PAMPS semibatch study. Each of the graphs shown reports results using a different concentration of the PAMPS component.
Figure 6B:
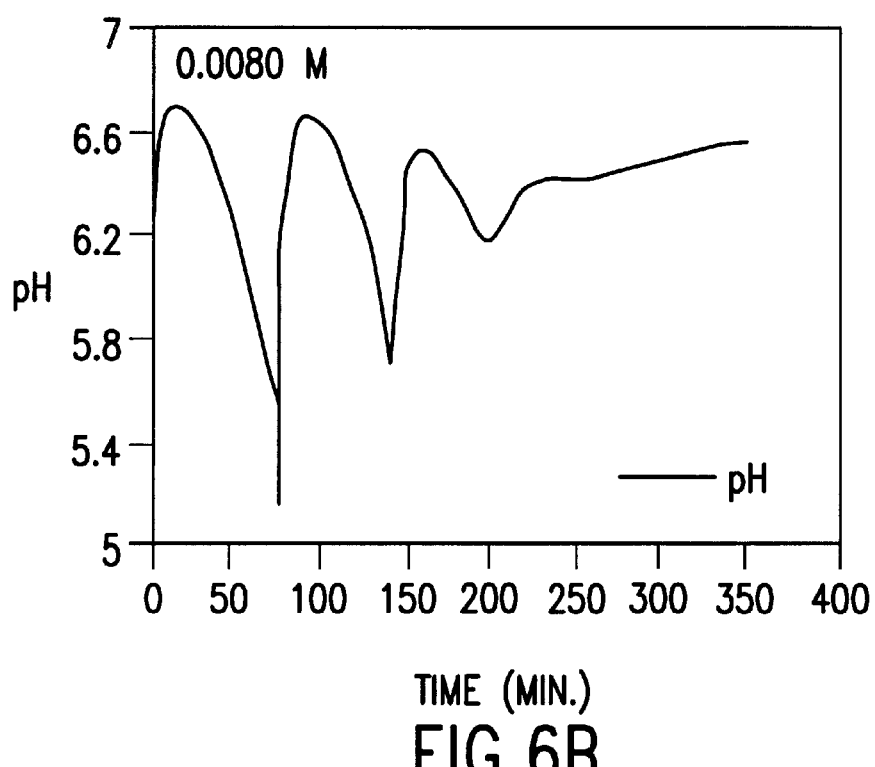
Figure 6C:
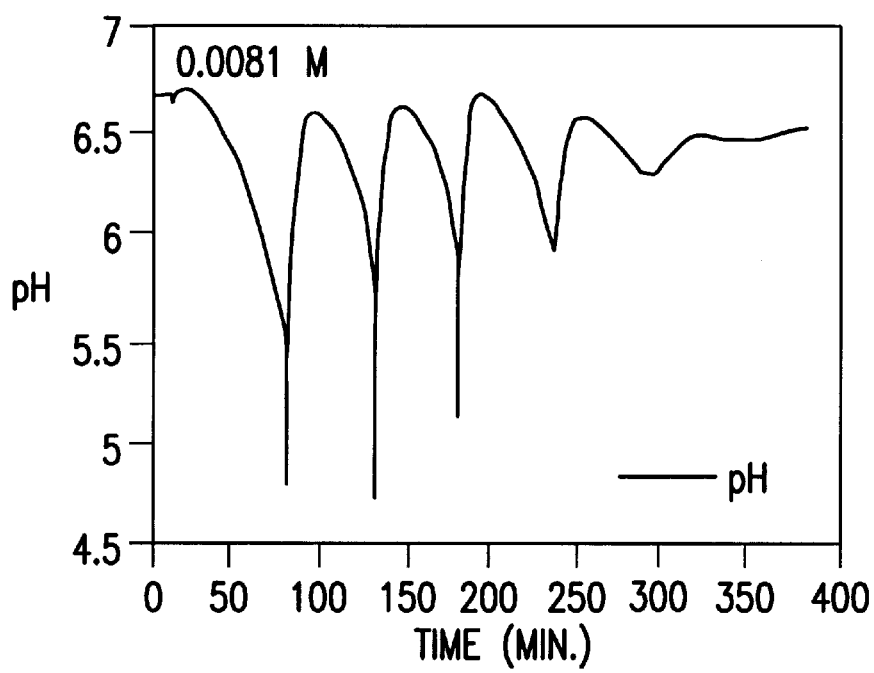
Figure 6D:
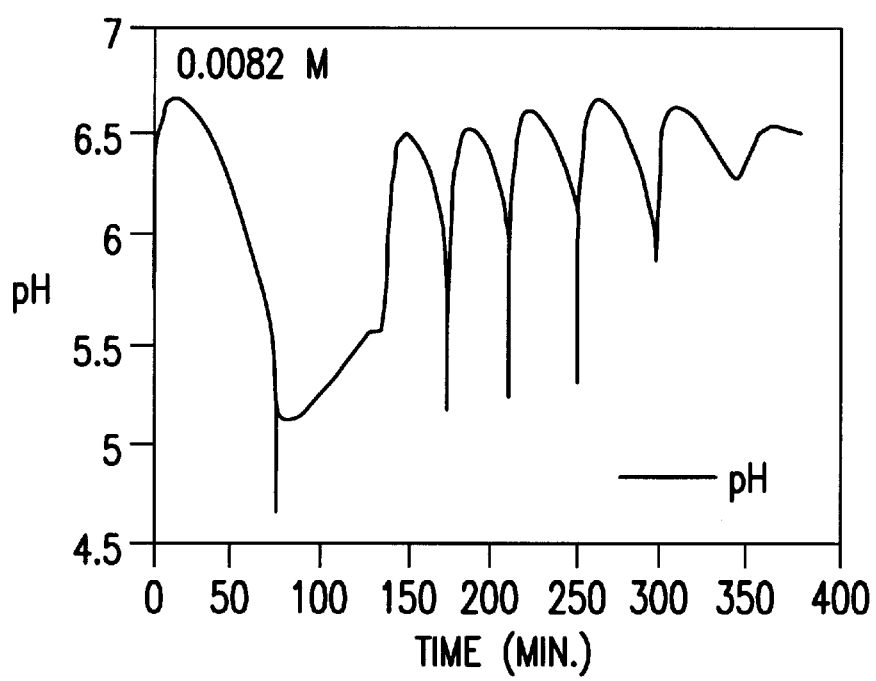
Figure 6E:
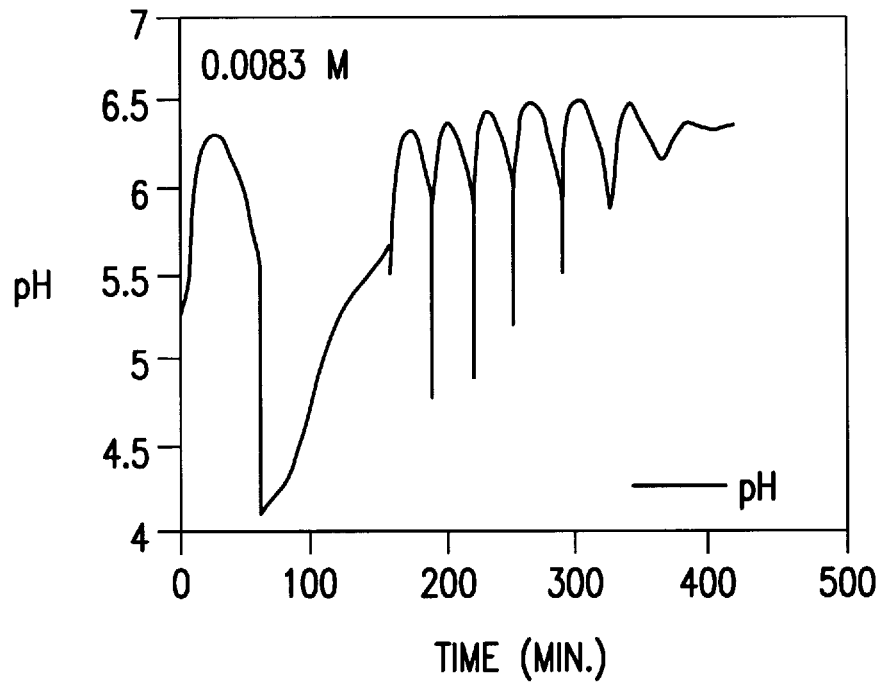
Figure 6F:
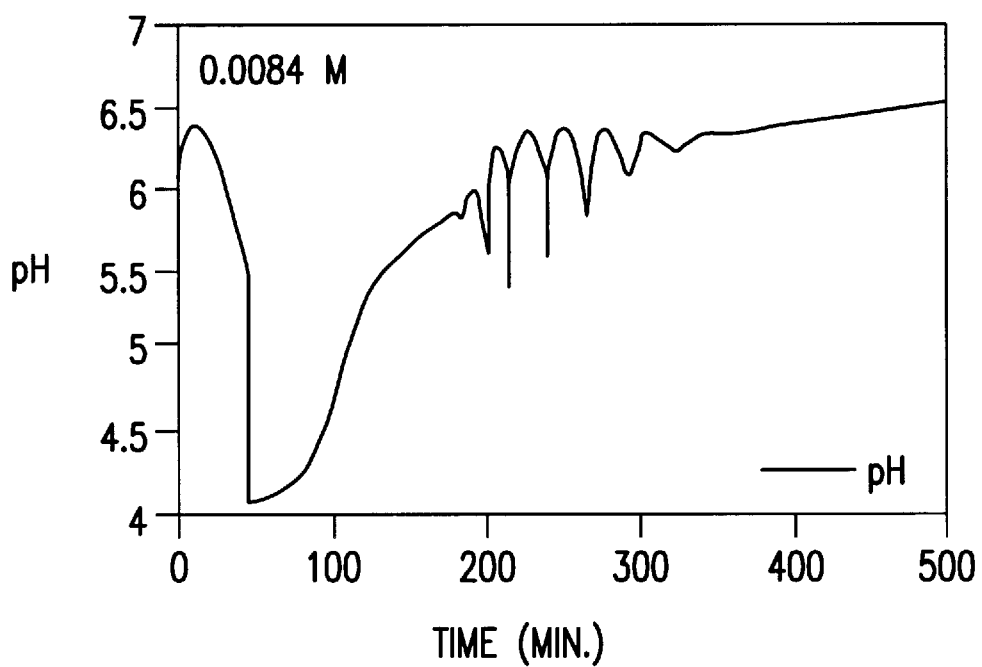
Figure 6G:
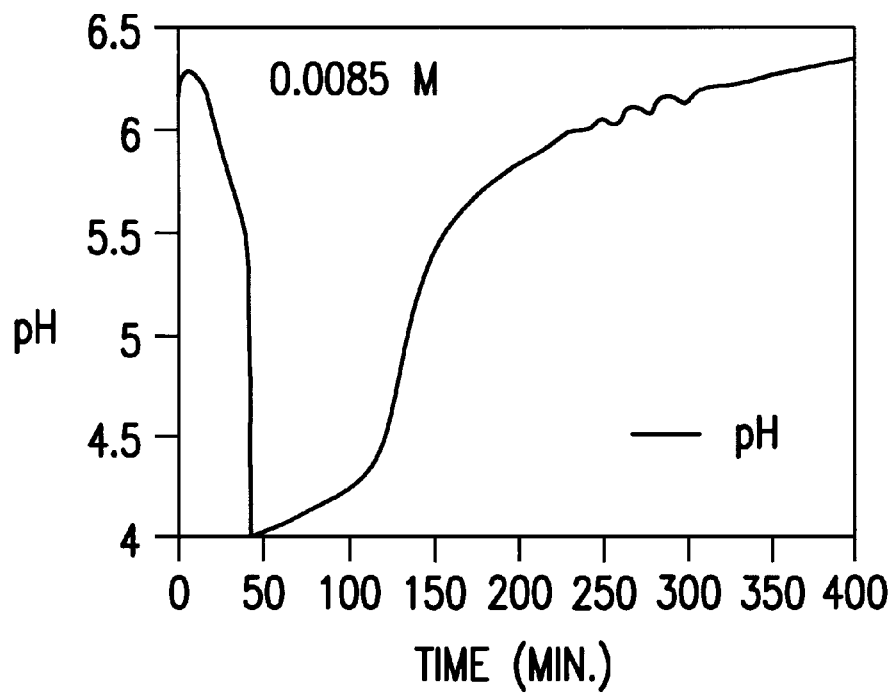
Figure 6H:
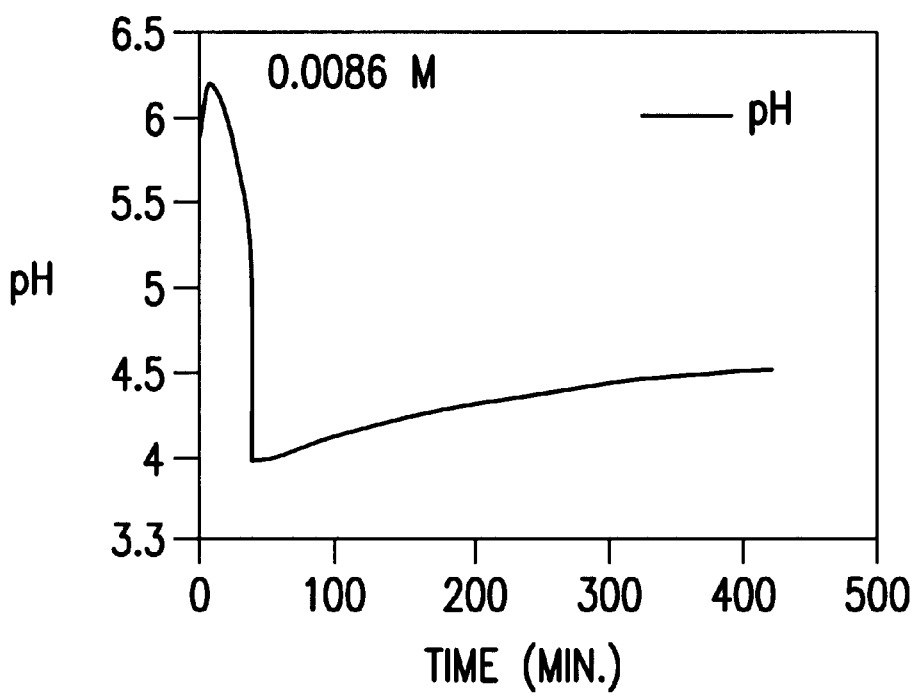
Figure 7A:
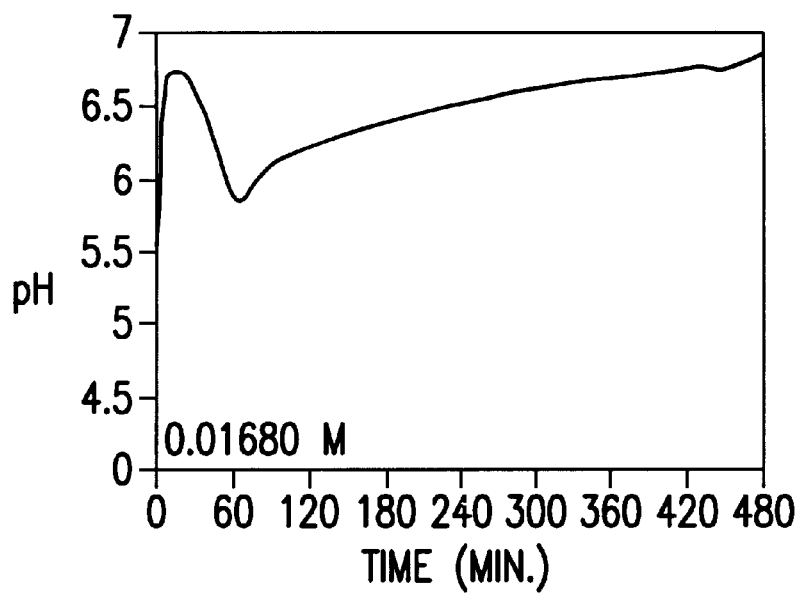
FIG. 7 shows the results of the Iodate-Sulfite-Thiosulfate-Nicotine semibatch study using various concentrations of sulfuric acid.
Figure 7B:
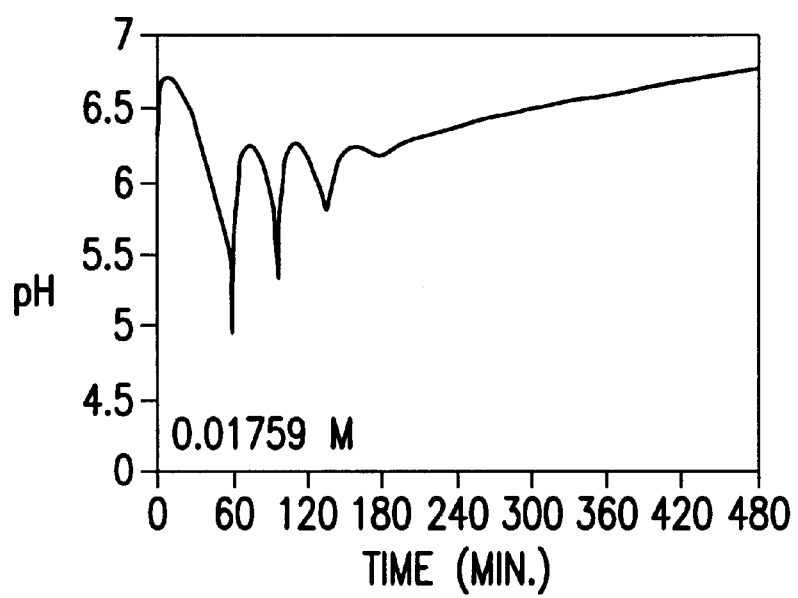
Figure 7C:
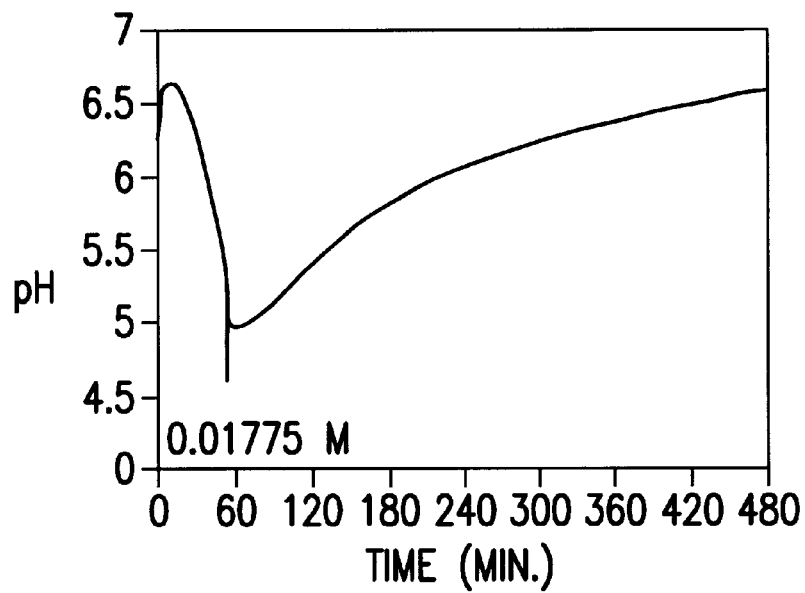
Figure 7D:
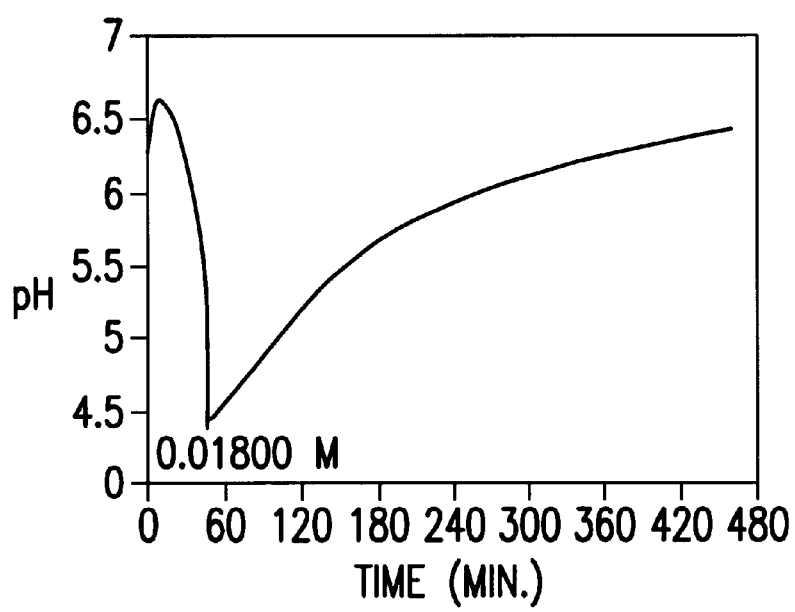

Iodate-Sulfite-Thiosulfate and PAMPS—Several water soluble polymers were tested as potential candidates for a viscosity enhancer within the iodate oscillator system. Poly (acrylic acid) gave encouraging results, but oscillations were not produced. Poly(2-acrylamido-2-methyl-1-propane sulfonic acid) 10 wt. % in water, (PAMPS) was found to be readily available from Aldrich Chemical Co. and in the free acid form. Other polymeric sulfonic acids are only available in the sodium salt form which would necessitate purification and characterization. This polymer has a pendent sulfonic acid group and recently has been studied by Gooda and Huglin (Gooda, S. R. and Huglin, M. B. J. of Polym. Sci. Part A, 30:1549–1557 (1992) and Gooda, S. R. and Huglin, M. B. Macromolecules, Vol. 25, No. 16, 4215–4217 (1992)). Initial experimentation revealed that pH oscillations were possible substituting PAMPS for sulfuric acid in the iodate oscillator (FIG. 5). Therefore, a study was conducted in order to identify oscillations as a function of the concentration of PAMPS, the results of which are shown in FIG. 6. The pH oscillates between 6.5 and 4.0, however, the pattern of oscillation is very sensitive to the concentration of PAMPS. This type of behavior is not uncommon in nonlinear systems. The amplitude and periodicity of the pH value changed significantly, as the concentration of PAMPS was varied from 0.0075 M to 0.0087 M in increments of 0.0001 M. Molarity of PAMPS was calculated based upon the repeat unit. When the PAMPS concentration was below the critical acid concentration, the pH stayed above 5.5 and oscillations could not be started. Conversely, when the PAMPS concentration was increased too much, the pH fell to 4.0 or below, stimulating the iodate-iodide reaction to occur and/or inhibiting the pH to return to 5.5. Therefore, at a concentration of 0.0080 M, there is enough available acid to allow oscillations. When the concentration is increased, the number of oscillations increase. Above the concentration of 0.0083 the reactor solution becomes acidic and oscillations are damped. In order to develop a usable drug delivery system, a viscosity modifier is required. Several synthetic and natural water soluble polymers are now under investigation. When poly (2-acrylamido-2-methyl-1-propane sulfonic acid) or PAMPS was directly substituted for sulfuric acid, pH oscillations of the same period and amplitude were observed. This is the first polymeric substitution that we know of in a chemical oscillating system where the polymer actively participates in the reaction instead of serving as an inert reaction medium. Recently, 2 articles by Prem Mohan (Drug Dev. Res. 29:1–17 (1993) and Drugs of the Future 1993, 18(4):351–358) discuss the potential use of sulfonic acid derivatives as selective anti-HIV-1 agents. PAMPS, the polymeric sulfonic acid that can be substituted for sulfuric acid in the iodate oscillator reaction, shows anti-HIV-1 activity. Other smaller sulfonic acids, which may be incorporated into the oscillator system, also show anti-HIV-1 activity.

Example 3 pH Oscillations in a Semibatch Reactor with a Drug

Iodate-Sulfite-Thiosulfate and Nicotine—The procedure used for the (−)-Nicotine experiments was a slightly modified version of the procedure above, in order to account for the sensitivity of nicotine free base to oxidation. A 40.0 mL aliquot of sulfuric acid stock solution was first measured into a 125 mL Erlenmeyer flask. 0.50 mL of (−)-nicotine free base was then measured using a disposable glass pipette and added to the sulfuric acid solution. It was assumed that the nicotine sulfate salt was formed immediately. Dry argon gas was used to flush the nicotine reagent bottle in order to avoid oxidative decomposition of the nicotine free base. 40.0 mL aliquots of the remaining two stock solutions (sodium sulfite, sodium thiosulfate) were then added to the 125 mL Erlenmeyer flask. This clear, colorless, homogeneous solution was then introduced, at 0.225 mL/min. using a peristaltic pump, into a 500 mL 3 neck round bottom flask containing 300 mL of 0.05 M sodium iodate. The reactor was at room temperature and the solution was mixed by magnetic stirring. Experimentation towards the incorporation of a pharmaceutically active compound into the iodate pH oscillator was then initiated. Nicotine was suggested as a model compound because: 1) it is miscible in water, 2) it forms stable salts with almost any acid, 3) the pKa's are 3.4 and 7.9 respectively for the deprotonation of the protonated pyridine and pyrrolidone nitrogens, 4) a vast amount of information is readily available concerning physicochemical properties and analytical techniques, and 5) nicotine permeation across synthetic and biological membranes is well documented. Nicotine (free base) was found to be compatible in the iodate system. It was assumed that the free base formed the sulfate salt upon addition to sulfuric acid. There was no discoloration of either the addition solution or reactor solution which indicates a minimum of nicotine oxidation. pH oscillations are shown in FIG. 7. It was assumed that the free base formed the sulfate salt upon addition to sulfuric acid. If nicotine is oxidized during the oscillator experiment, the most probable products are S-Cotinine and S-Nicotine-N'-Oxide, which are reported to be colorless. Shown in FIG. 7, are the results of a study investigating the addition of nicotine free base to the iodate oscillator. When nicotine is added, the system becomes even more sensitive to variation in species concentration. In this study only the acid concentration was varied. pH Oscillations were observed, but are very sensitive to the amount of each component and laboratory techniques, which seem to account for the difficulty in achieving oscillations.

Additional experimentation with the combination of nicotine free base and PAMPS revealed no solution discoloration or polymer precipitation in the iodate oscillator system. This suggests that both PAMPS and nicotine (free base) are compatible.

Figure 8A:
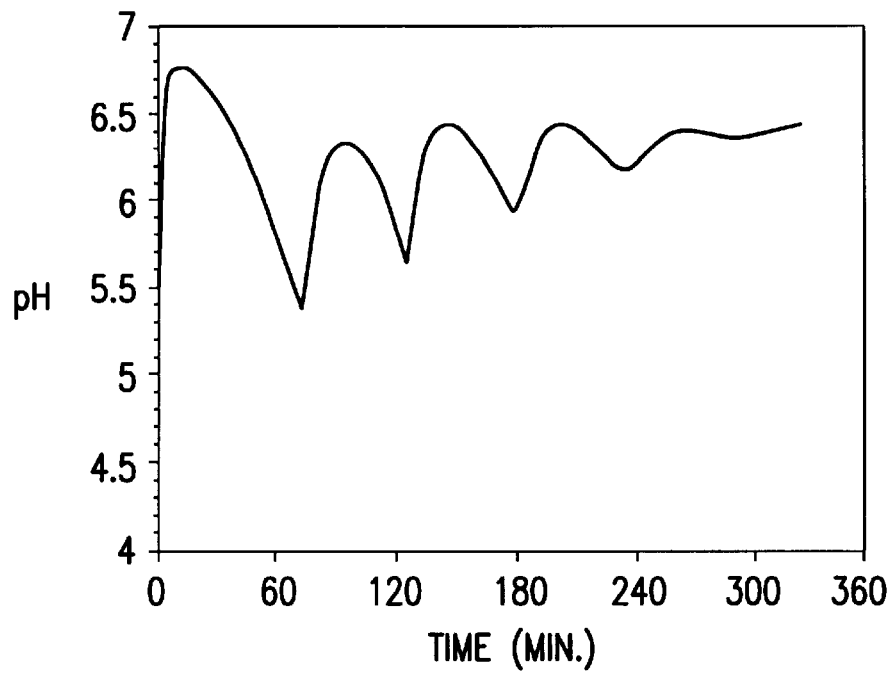
FIG. 8 shows the results of the Iodate-Sulfite-Thiosulfate-Sodium Benzate semibatch study under conditions where Solution A (0.02 M $Na_2SO_3$, 0.015 M $Na_2S_2O_3$, 0.005 M $H_2SO_4$ and 0.02047 M sodium benzoate) is introduced into 300 mL of Solution B (0.05 M $NaIO_3$) at 0.225 mL/min.
Figure 8B:
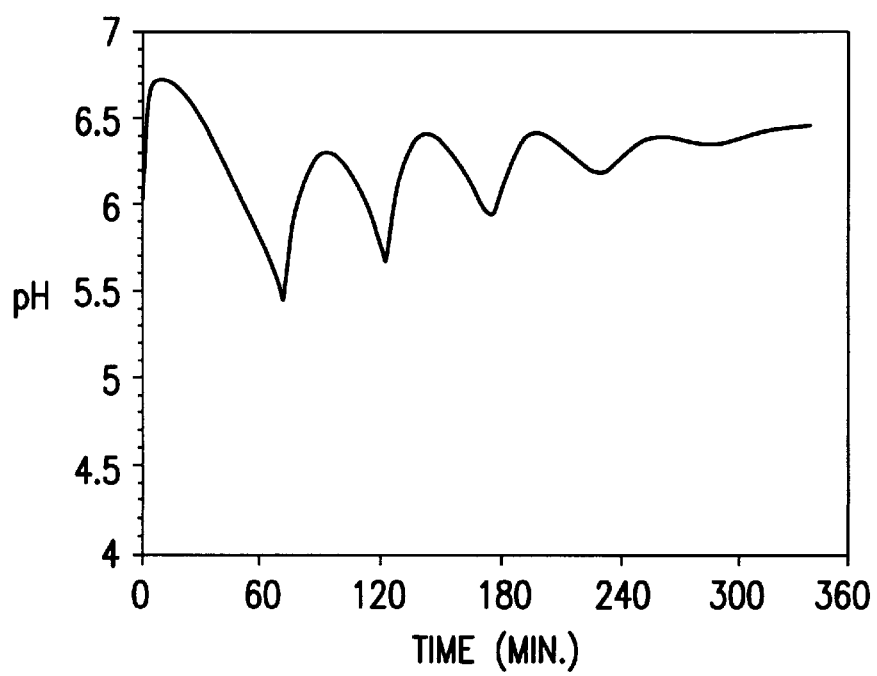

Iodate-Sulfite-Thiosulfate and Sodium Benzoate—Benzoic acid has been investigated as a model compound to demonstrate the application of pH oscillators to modulate the delivery of the ingredient. Experimentation revealed the repeatable production of pH oscillations when sodium benzoate is added in the iodate oscillator system (see FIG. 8). This suggests that benzoic acid is compatible in the iodate system and benzoic acid can be released in a temporal fashion.

Example 4

Determination of Permeated Benzoate Ion at Constant pH Values

Following the methods described by Morimoto et al. (Morimoto et al., Chem. Pharm. Bull. 39(9):2412–2416 (1991)), a modified assay method was developed for the determination of benzoic acid permeation across EVA membranes at constant pH values. Additional methodology has been taken from Maurin (Maurin, M. B., Dittert, L. W., Hussain, A. A. J. Pharm. Sci. Vol. 81, No. 1 (1992)). The permeation of a model compound (benzoic acid) across a model membrane (28% EVA, 2 mil thick, 32 C) was characterized at discrete pH values. Table 2 expresses the actual concentration of permeate through the membrane and the corresponding flux. The donor solution was 0.05 M sodium iodate with 0.02047 M sodium benzoate. The pH was adjusted with the addition of sulfuric acid. The receiver solution was 0.05 M phosphate buffer (pH 2.4). The resulting flux was greater than expected owing to the fact that the temperature was increased and a higher vinyl acetate content (EVA, 28% vinyl acetate content, film of 2 mil thickness was used rather than 25% EVA). This agrees with Maurin (1992). FIG. 9 shows the steady state flux of benzoate that diffused through the 5 $cm^2$ of 28% EVA film at different pH values.

TABLE 2

| FLUX OF BENZOATE ION THROUGH 2 mil EVA (28%) MEMBRANE | | |
|---|---|---|
| pH | CONCENTRATION | FLUX (mcg/min/$cm^2$) |
| 6.5 | 0.17 | 0.008 |
| 6.0 | 0.44 | 0.020 |
| 5.5 | 1.50 | 0.070 |
| 5.0 | 3.90 | 0.195 |
| 4.5 | 9.50 | 0.480 |

Example 5

Determination of Permeated Benzoate Ion at Oscillating pH Values

Figure 11A:
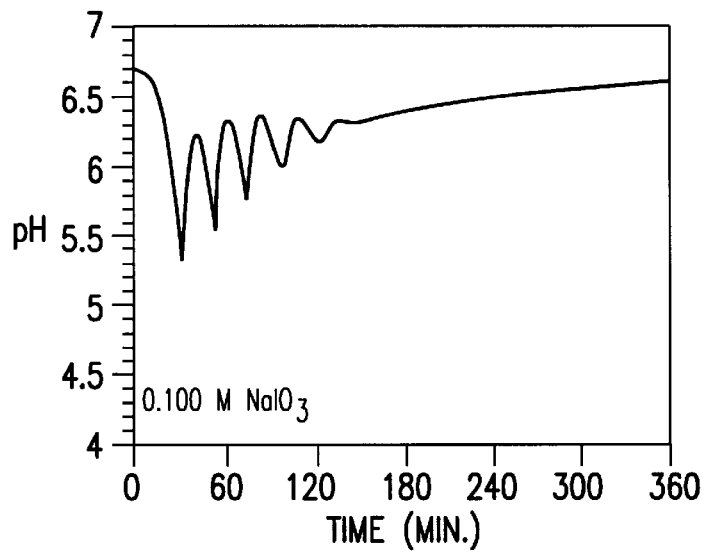
FIG. 11 illustrates changes in period frequency due to changes in iodate concentration resulting from semibatch iodate experiments. The period frequency increases as the iodate concentration increases.
Figure 11B:
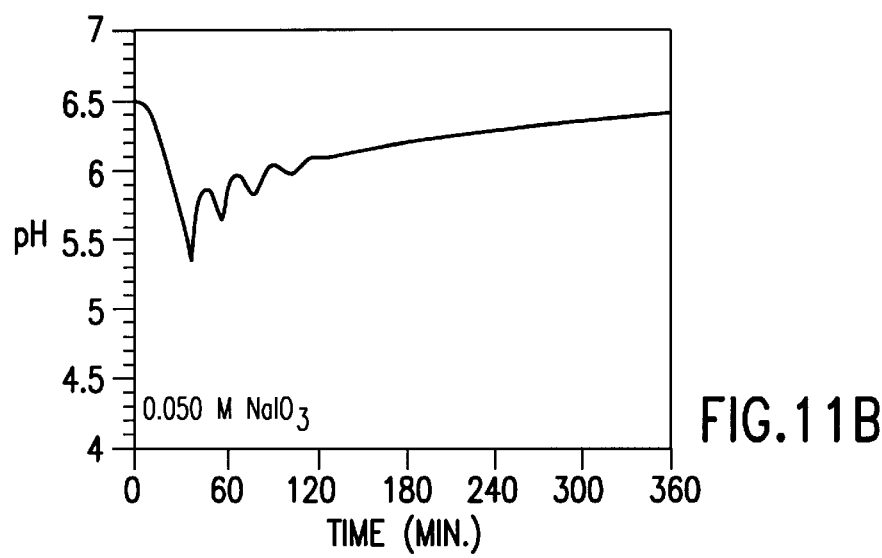
Figure 11C:
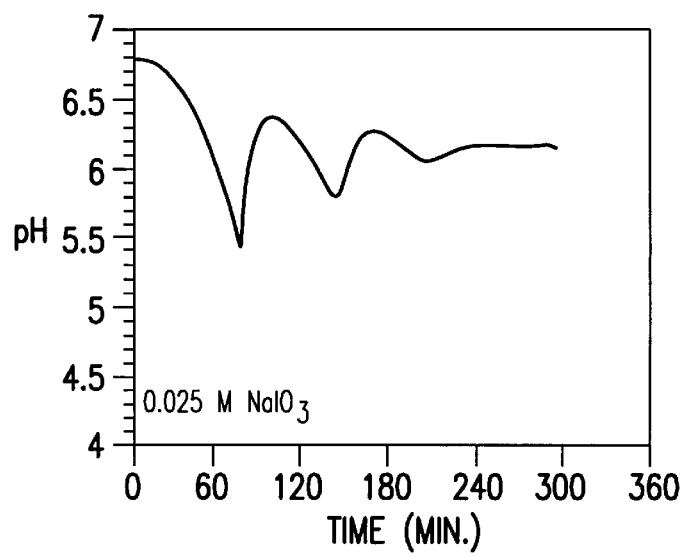
Figure 12A:
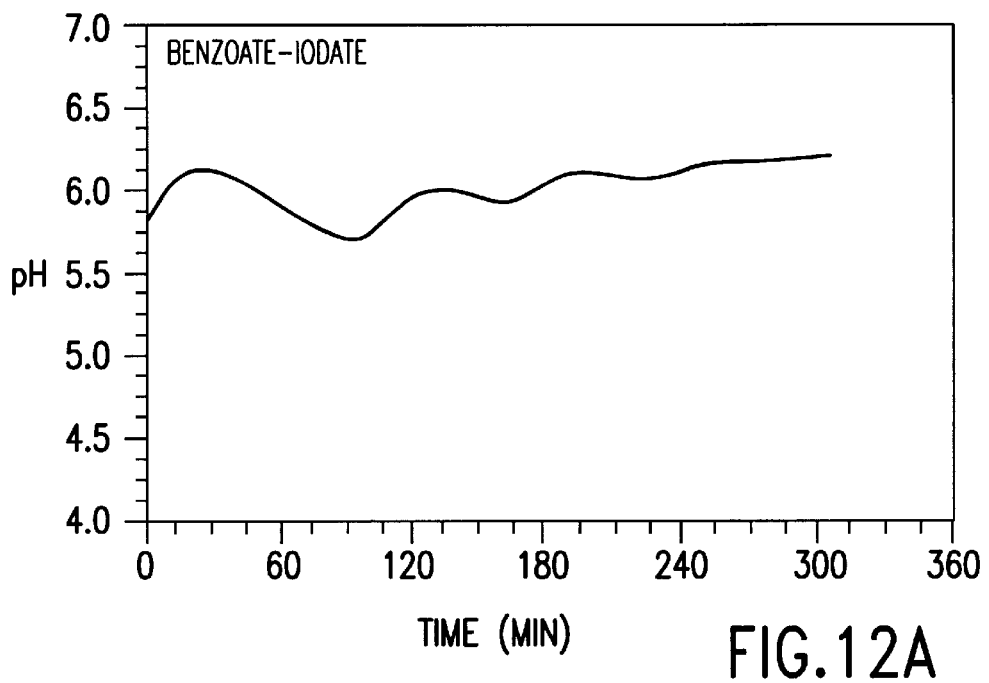
FIG. 12 shows pH oscillation of the iodate system under semibatch conditions using the benzoic acid/benzoate permeant model. Conditions are as indicated in Example 4 and Table 2.
Figure 12B:
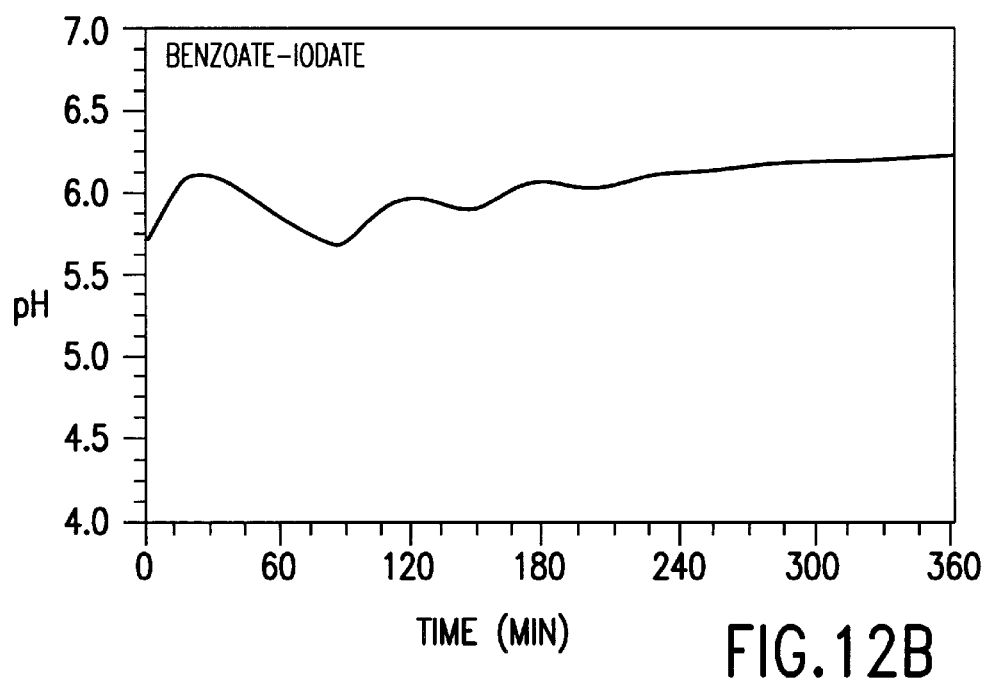
Figure 12C:
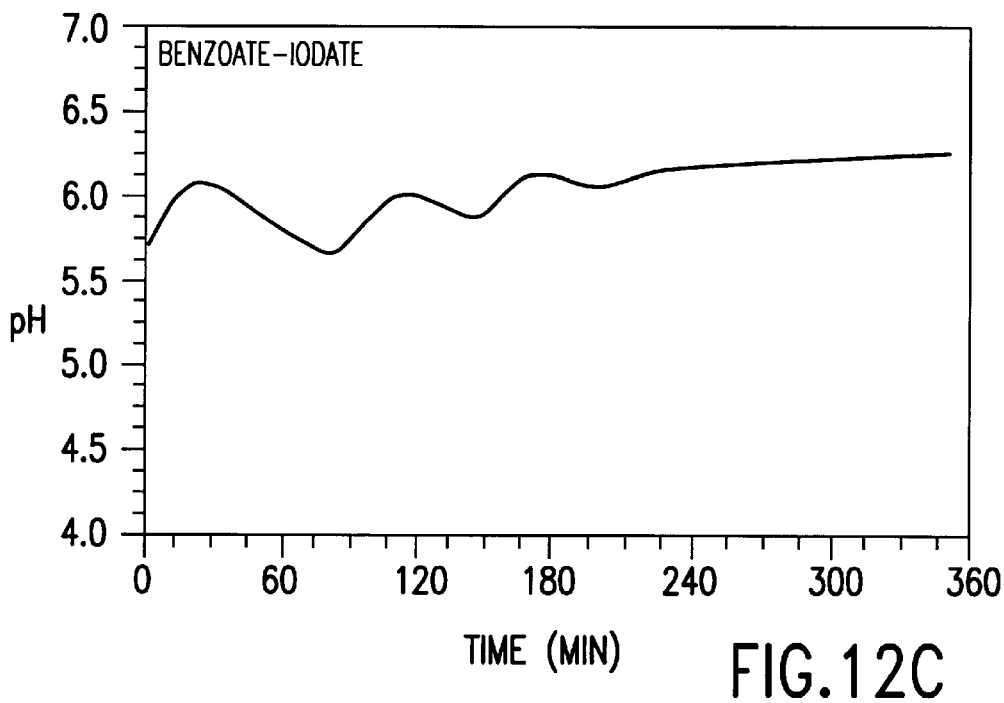
Figure 12D:
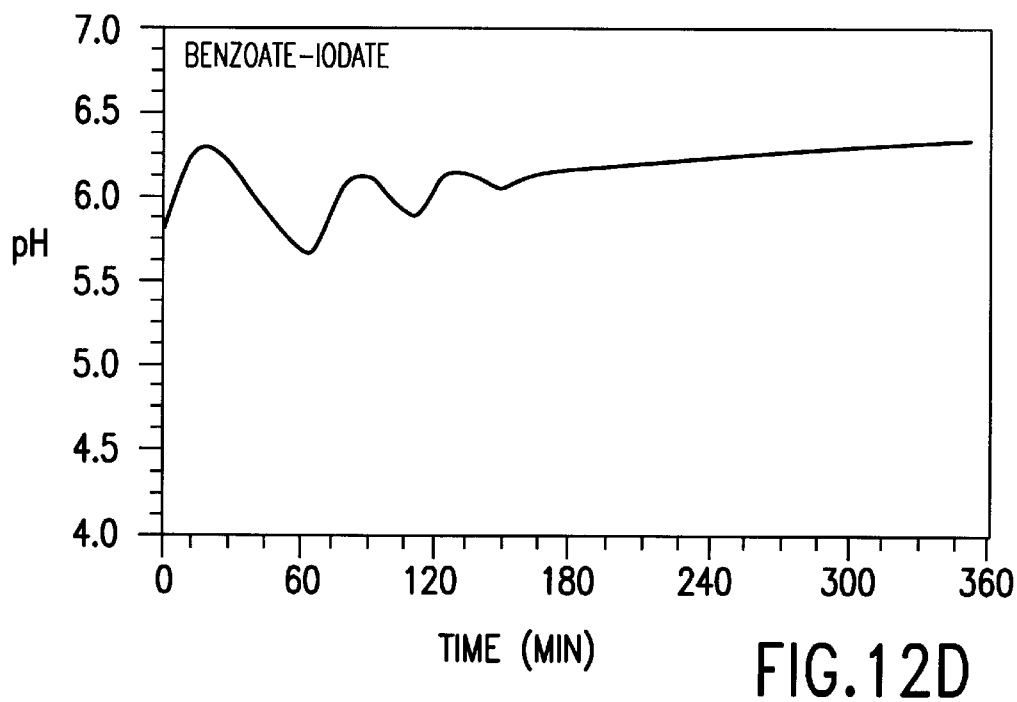
Figure 12E:
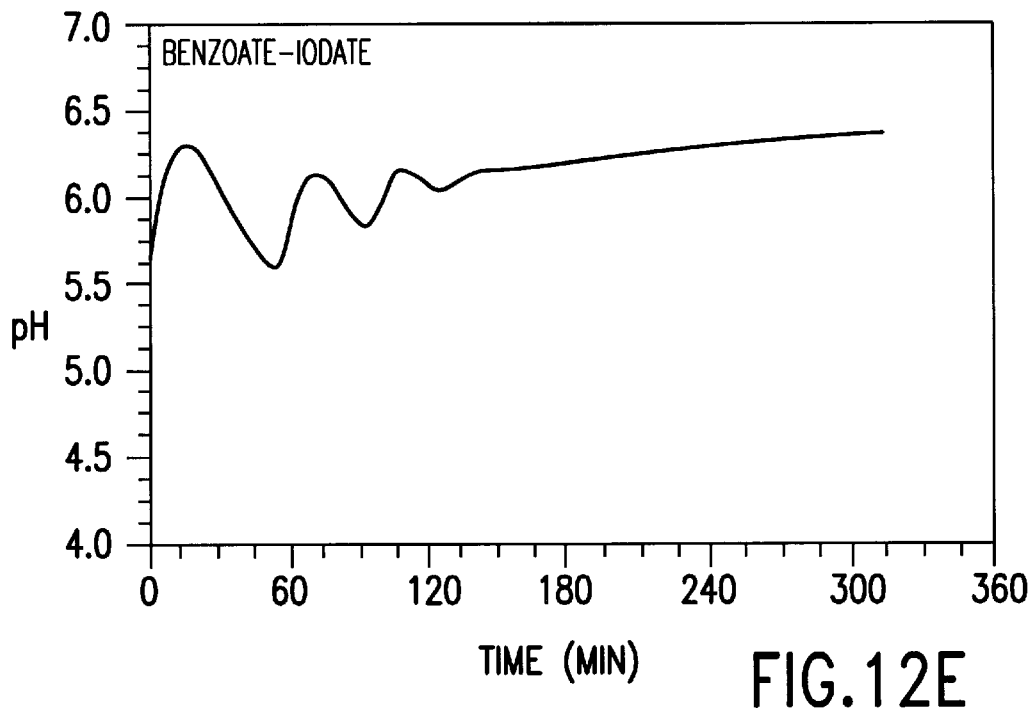
Figure 12F:
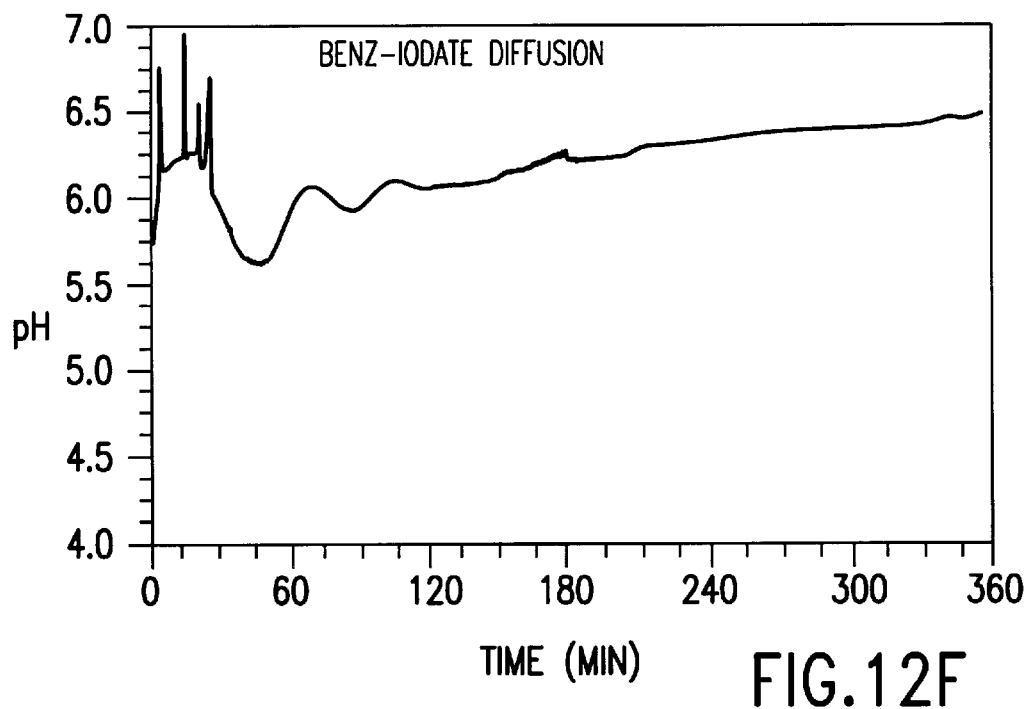

A. The periodicity of the pH oscillations in an iodate system (the mixed Landolt system) were first evaluated for further use in evaluating benzoate ion permeation under semibatch conditions. Steady and repeated oscillations were obtained. The results, shown in FIG. 11, indicate that the periodicity of the pH oscillations is a function of the iodate concentration and that the frequency of the oscillation increases with increasing iodate concentration. Based on this data, 0.025 M Iodate concentration was used for the balance of this experiment.

B. For these experiments, a 2 mil, 28% ethylene/vinyl acetate (EVA) membrane was employed. The model active agent (benzoic acid, 0.02047 M) was placed in an iodate solution and the pH was adjusted to a value of 5.8 using sodium hydroxide. A sulfoxide addition solution containing sulfuric acid, sodium sulfite, and sodium thiosulfate in a ratio of 1:4:3 was added at a rate of 0.225 mL/min. The specific concentrations of the sulfoxide component are shown in Table 3 below.

TABLE 3

| CONCENTRATION OF REACTANTS USED TO OBTAIN GRAPHS IN FIG. 12 A–F | | | | |
|---|---|---|---|---|
| GRAPH | IODATE | SULFURIC ACID | SULFITE | THIOSULFATE |
| A (1X) | 0.025 M | 0.00504 M | 0.020 M | 0.0150 M |
| B | 0.025 M | 0.00533 M | 0.021 M | 0.0160 M |
| C | 0.025 M | 0.00600 M | 0.024 M | 0.0180 M |

TABLE 3-continued

CONCENTRATION OF REACTANTS USED TO OBTAIN GRAPHS IN FIG. 12 A–F

| GRAPH | IODATE | SULFURIC ACID | SULFITE | THIOSULFATE |
|---|---|---|---|---|
| D (2X) | 0.025 M | 0.01000 M | 0.040 M | 0.0300 M |
| E (2.5X) | 0.025 M | 0.01250 M | 0.050 M | 0.0375 M |
| F (3X) | 0.025 M | 0.01500 M | 0.060 M | 0.0450 M | pH oscillations were consistently obtained. The results, shown in FIG. 12, indicate that the amplitude as well as the periodicity of the pH oscillations are a function of sulfoxide concentration in this case. At three times (Table 3, F) the normal concentration (Table 3, A), the system was overloaded and the rate of addition reduced.

C. In the flux experiment, a 2 mil, 28% EVA film was used at 32° C. with semibatch conditions. a 75 mL donor cell was used. The sulfoxide solution contained 0.02 M sodium sulfite, 0.015 M sodium thiosulfate and 0.005 M sulfuric acid, with 0.02047 M sodium benzoate and was added to a 0.025 M sodium iodate solution at the rate of 0.225 mL/min using a peristaltic pump. The results indicate that the flux of benzoate responds to pH changes, increasing as pH decreases while decreasing when pH increases.

Figure 14A:
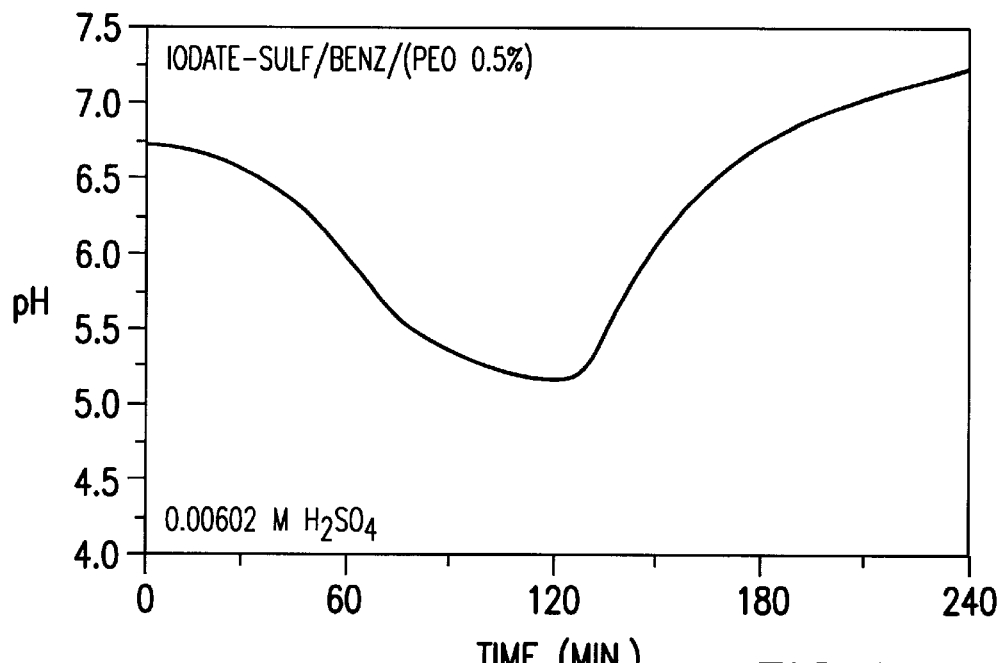
FIG. 14 illustrates pH oscillations under semibatch conditions using a 100 mL, 3 neck, round bottom flask in the presence of additional thickener, under conditions where Solution A (0.05 M sodium iodate) is introduced into 80 mL of Solution B (0.02 M $Na_2SO_3$, 0.015 M $Na_2S_2O_3$ with either 0.00602 M $H_2SO_4$ (FIG. 14A) or 0.01175 M PAMPS (FIG. 14B), 0.02047 M sodium benzoate and 0.5% poly (ethyleneoxide) (PEO) (4,000,000 MW)) at 0.080 mL/min using a peristaltic pump.
Figure 14B:
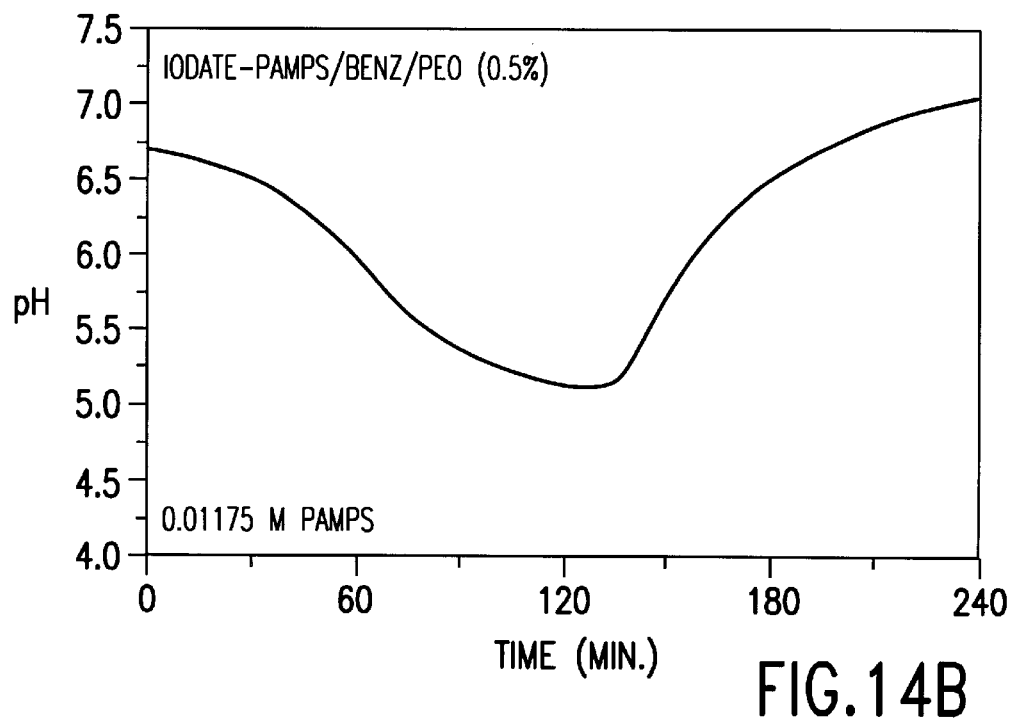

D. A variation of the experiment C above (results shown in FIG. 14), began with approximately 20% of the benzoate added to the iodate solution. Upon this addition, the pH of the iodate solution rose to 7.6, which was adjusted to 5.84 with a small amount of sulfuric acid. The addition rate of the iodate solution was 0.11 mL/min, but otherwise the conditions were the same as in C above. The profile obtained shows a shorter lag time and a clearer response of active agent diffusion to pH oscillation is seen.

E. The variation in this experiment was basically the inclusion of all of the benzoate in the iodate solution. This differed from C above in that the sulfoxide solution contained 0.06 M sodium sulfite, 0.045 M sodium thiosulfate and 0.015 M sulfuric acid, while the iodate solution contained 0.025 sodium odate and 0.02047 M benzoic acid. The iodate solution was added to the sulfoxide solution at a rate of 0.175 mL/min using a peristaltic pump. The results show elimination of the initial time lag (seen in C and D above) and benzoate diffusion responding to pH (increasing diffusion when pH decreases and decreasing when pH increases).

Figure 13:
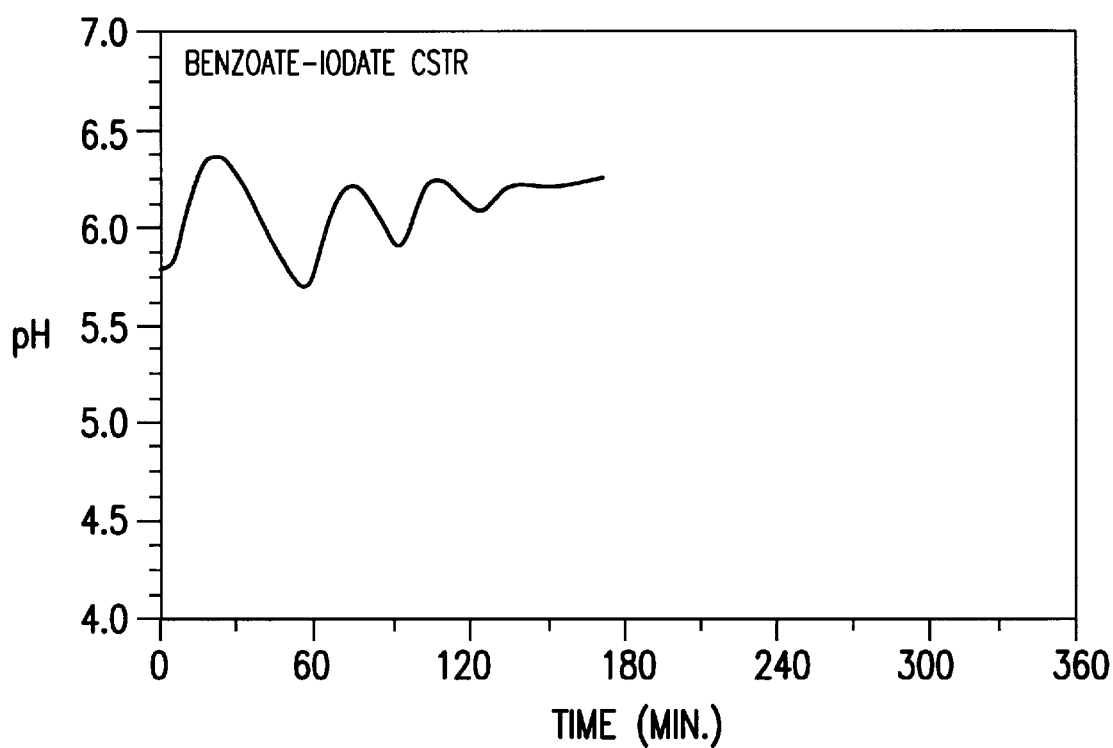
FIG. 13 illustrates pH oscillations in the presence of benzoate in a continuous-flow stirred tank reactor (CSTR) using 3 mil 19% EVA film at 24° C. and a 75 mL Crown donor cell. Solution A (containing 0.06 M $Na_2SO_3$, 0.045 M $Na_2S_2O_3$ and 0.01512 M $H_2SO_4$) is added to solution B (0.025 M sodium iodate and 3.0 mg/mL of benzoic acid) at 0.190 mL/min using a peristaltic pump, pH=5.80; Solution B is added at 0.095 mL/min.

Example 6 pH Oscillations Under CSTR Conditions 4 trials of the same system were run under CSTR conditions using a 3 mil, 19% EVA membrane and a 75 mL Crown Donor Cell. The concentrations and rate of addition are specified in Table 4 below. The results obtained with sample D are reported in FIG. 13. In all cases, solution (a) below is added to solution (b).

TABLE 4

| SAMPLE REACTANT TEMPERATURE | A 24° C. | B 21.5° C. | C 20° C. | D 24° C. |
|---|---|---|---|---|
| a.) | | | | |
| Na$_2$SO$_3$ | 0.05 M | 0.05 M | 0.05 M | 0.06 M |
| Na$_2$S$_2$O$_3$ | 0.0375 M | 0.0375 M | 0.0375 M | 0.045 M |
| H$_2$SO$_4$ | 0.0126 M | 0.0132 M | 0.01322 M | 0.01512 M |
| b) | | | | |
| NaIO$_3$ | 0.025 M | 0.025 M | 0.025 M | 0.025 M |
| benzoic acid | 3.0 mg/mL | 3.0 mg/mL | 3.0 mg/mL | 3.0 mg/mL |
| rate of (a) added to (b) | 0.150 mL/min | 0.190 mL/min | 0.190 mL/min | 0.190 mL/min |
| rate of (b) addition | 0.075 mL/min | 0.095 mL/min | 0.095 mL/min | 0.095 mL/min |

Example 7

Effect of Reversal of Order of Adding Reactants

Figure 15:
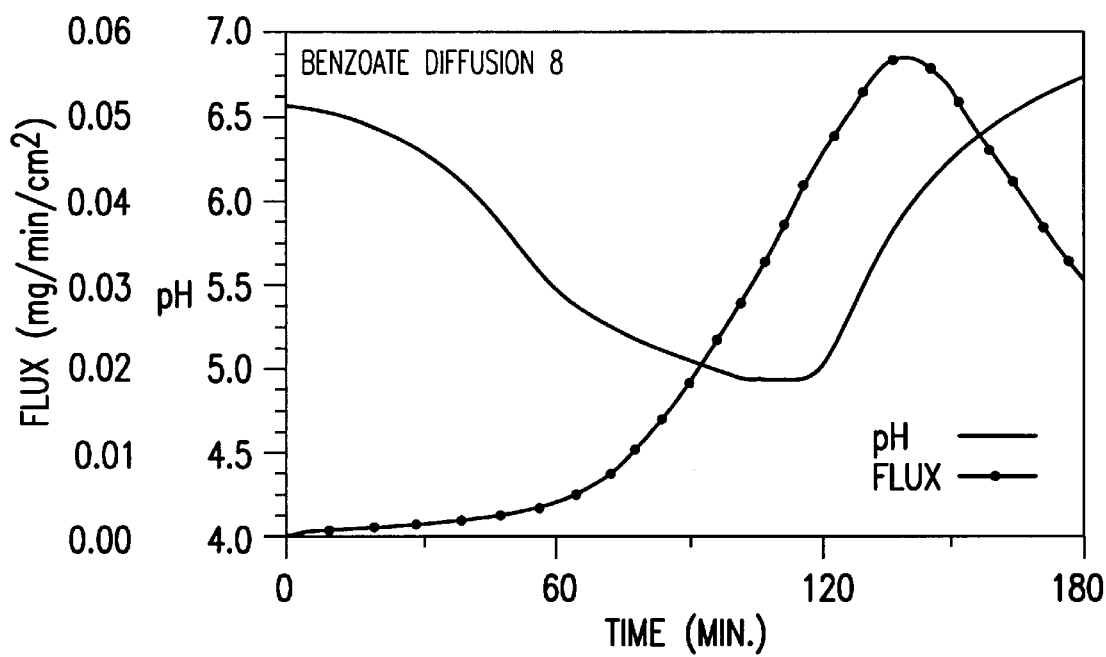
FIG. 15 demonstrates the semibatch flux of benzoate and the pH variation due to adding iodate to sulfoxide, rather than sulfoxide to iodate, utilizing 2 mil 28% EVA film at 32° C. and a 75 mL donor cell in which Solution A (0.05 M sodium iodate) is introduced to 75 mL of Solution B (0.02 M $Na_2SO_3$, 0.015 M $Na_2S_2O_3$ with 0.00604 M $H_2SO_4$ and 0.02047 M sodium benzoate) at 0.080 mL/min using a peristaltic pump.
Figure 16:
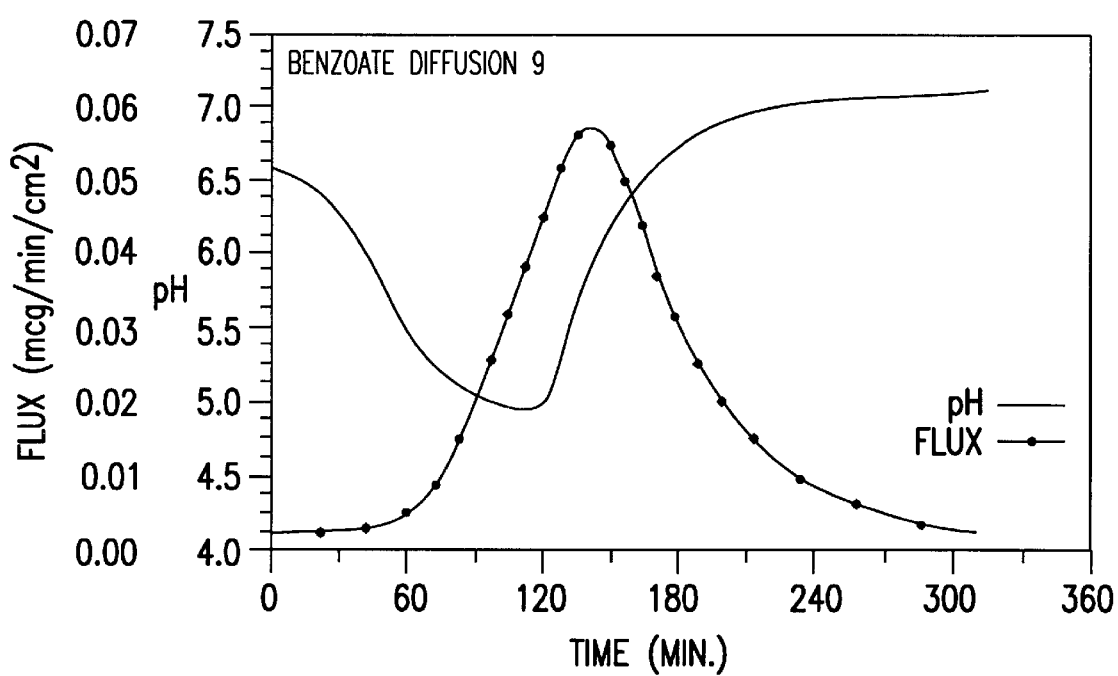
FIG. 16 illustrates benzoate diffusion under semibatch conditions in response to pH oscillations utilizing 2 mil 28% EVA film at 32° C. and a 75 mL donor cell in which Solution A (0.05 M sodium iodate) is introduced to 75 mL of Solution B (0.02 M $Na_2SO_3$, 0.015 M $Na_2S_2O_3$ with 0.00604 M $H_2SO_4$ and 0.02047 M sodium benzoate) at 0.080 mL/min using a peristaltic pump.

This experiment was run using semibatch conditions with a 2 mil, 28% EVA film at 32° C. and a 75 mL donor cell. 0.05 M sodium iodate (solution A) was introduced into 75 mL of a sulfoxide solution containing 0.02 M sodium sulfite, 0.015 M sodium thiosulfate, 0.00604 M sulfuric acid and 0.02047 M sodium benzoate at a rate of 0.080 mL/min using a peristaltic pump. The results are shown in FIG. 15. The reversal of the order of addition results in a single period. The presence of all of the benzoate in the solution which is added, allows all of the benzoate present to react to the changes in environment, which is that as pH decreases, the benzoate flux increases, and as pH increases, the benzoate flux decreases. A 20 minute diffusional lag is also seen which is relative to the permeation of benzoate through EVA membrane.

Example 8

Figure 17:
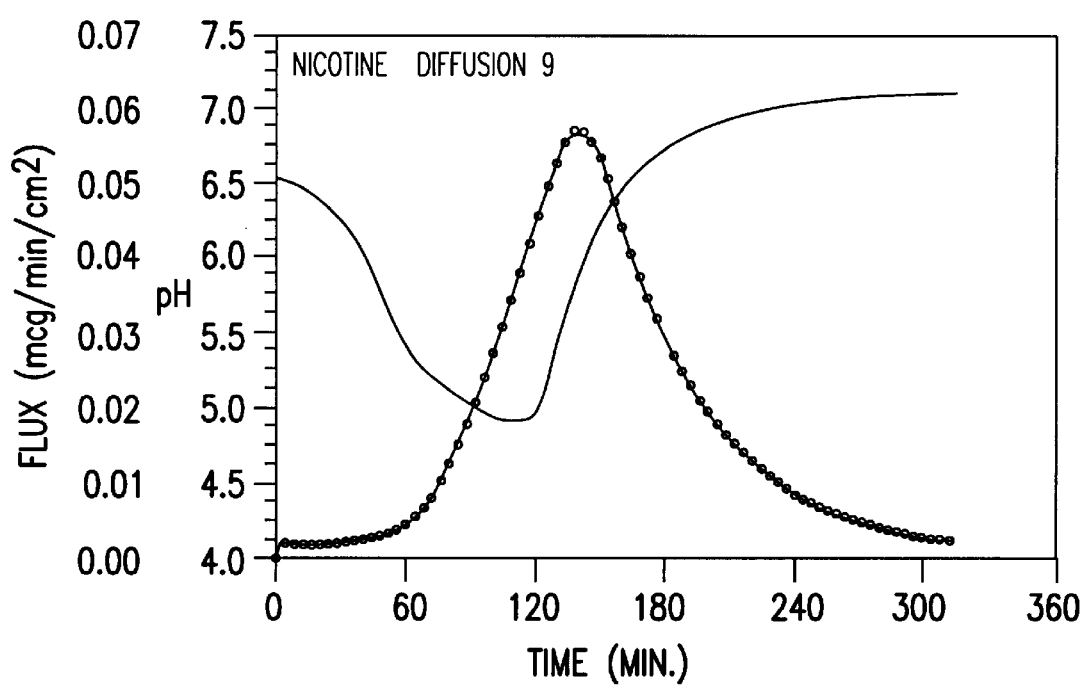
FIG. 17 illustrates nicotine diffusion under semibatch conditions in response to pH oscillations utilizing 2 mil 28% EVA film at 32° C. and a 75 mL donor cell in which Solution A (0.05 M sodium iodate) is introduced to 75 mL of Solution B (0.022M $Na_2SO_3$, 0.015 M $Na_2S_2O_3$ with 0.03797 M $H_2SO_4$ and 0.7 mL nicotine free base) at 0.080 mL/min using a peristaltic pump.

This experiment was run using semibatch conditions with a 2 mil, 28% EVA film at 32° C. and a 75 mL donor cell. 0.05 M sodium iodate (solution A) was introduced into 75 mL of a sulfoxide solution containing 0.021 M sodium sulfite, 0.015 M sodium thiosulfate, 0.03797 M sulfuric acid and 0.75 mL of nicotine free base at a rate of 0.080 mL/min using a peristaltic pump. The results are shown in FIG. 17. In this experiment the donor solution is allowed to stand for 60 minutes in order for the nicotine to passively diffuse across the membrane.

After this time period, the iodate solution is added and the oscillation reaction begun. The reversal of the order of addition results in a single period. The presence of all of the nicotine in the solution which is added, allows all of the nicotine present to react to the changes in environment, which is that as pH decreases, the nicotine flux decreases, and as pH increases, the nicotine flux increases. A 30 minute diffusional lag is also seen which is relative to the permeation of nicotine through EVA membrane.

While various embodiments have been described with reference to the drawings, many other variations will be apparent to those of ordinary skill in the art without departing from the spirit of the instant invention. The description of the embodiments is therefore only intended to illustrate the general concept underlying the instant invention and not to limit the scope of the invention.

We claim:

1. A transdermal delivery device for the passive, temporal or periodic control of delivery of active agents, comprising:
   a) a first species, which is an active agent, to be delivered from said transdermal device or a second species to be modified in situ into said first species,
   b) some or all of the initial reactants of an oscillation reaction such that said oscillation reaction is not initiated until desired; and
   c) means for separating at least one of said initial reactants from the remainder of said initial reactants prior to activation of said oscillation reaction within said transdermal device when all of said initial reactants are contained within said transdermal device prior to activation or means for introducing any of said initial reactants of said oscillation reaction which are not otherwise present in said transdermal device prior to activation;
   whereby said oscillation reaction can be activated by bringing together all of said initial reactants or exposing said initial reactants to an activating condition and said delivery of said first species is passively controlled in response to said oscillations of said oscillation reaction.

2. The device of claim 1, wherein said oscillation reaction has an initial oscillation frequency, the delivery of said active agent is sensitive to at least one reactant or product of said oscillating reaction and said oscillation frequency corresponds to an oscillation period which is no less than 1.5 times the time period necessary for a deliverable species of said active agent to be delivered under the conditions of the oscillating reaction which permit such species delivery, said delivery occurring passively once said oscillating reaction is activated.

3. The device of claim 1 wherein said oscillation reaction is a pH oscillation reaction.

4. The device of claim 1 wherein said pH oscillation reaction is selected from the group consisting of iodate-sulfite-thiourea, iodate-sulfite-thiosulfate, iodate sulfite-ferrocyanide, iodate-hydroxylamine, periodate-hydroxylamine, periodate-thiosulfate, hydrogen peroxide-ferrocyanide, hydrogen peroxide-thiosulfate-copper(II), hydrogen peroxide-bisulfite-thiosulfate, peroxodisulfate-thiosulfate-copper(II), bromite-iodide, bromate-sulfite-ferrocyanide, bromate-sulfite-thiosulfate, and manganese (II)-periodate.

5. The device of claim 1 wherein said active agent is selected from the group consisting of pharmaceutically active agents and cosmetic active agents.

6. The device of claim 5 wherein said pharmaceutically active agents are selected from the group consisting of adrenergics, antiasthmatics, antiarrhythmics, anticancer drugs, anti-AIDS medications, anti-parkinsonian drugs, anti-anginals, Alzheimer's medications, somatomedins, anti-viral agents, antisense peptides, anti-ulcer medications, PMS therapeutics, analgesics, endocrine/reproductive therapeutics, birth control medicaments, general hormone replacement therapeutics, stroke medications, antibiotics, immunizations, addiction treatments, anxiolytics, antisensitization drugs, antiirritants, contrast media, and antiinflammatories.

7. The device of claim 6 wherein said pharmaceutically active agent is selected from the group consisting of LHRH, PTH, PTH fragments, PTH analogs, somatistatin, somatistatin analogs, melatonin, insulin, IGF-I, nicotine, nitrosoureas, steroids, gastric acid inhibitors, nitrates, beta-blockers, progesterone, aldactone, seratonin, melatonin, sleep-inducing peptides, DHEA, NSAIDS, BMP, and ACTH.

8. The device of claim 2 wherein said active agent delivery sensitivity to said oscillation reaction is the result of at least one of:
   a) said active agent changing a deliverable species and a substantially non-deliverable or non-deliverable species in response to said oscillation reaction oscillations;
   b) said delivery system further containing a barrier to said active agent delivery and said barrier changing between an active agent transmissible or releasable form and a substantially non-transmissible or non-releasable form or a non-transmissible or non-releasable form in response to said oscillation reaction oscillations;
   c) said delivery system containing a viscosity enhancer, said viscosity enhancer changing between species which are more and less soluble, swellable, or viscous in response to said oscillation reaction oscillations, whereby available solvent for dissolution of said active agent is altered correspondingly, so that transportability of said active agent and/or concentration of active agent are modified in response to said oscillations of said oscillating active agent;
   d) said delivery system optionally further comprises a flux enhancer or delivery aid which flux enhancer or delivery aid changes between an enhancing form (delivery-aid form) and a non-enhancing (non-delivery-aid form) in response to said oscillation reaction oscillations whereby the delivery of active agent is modified in response to said oscillation reaction oscillations; and
   e) said delivery system further comprises i) a flux enhancer or delivery aid and ii) a separation barrier which separates said flux enhancer or delivery aid from said active agent, wherein said separation barrier changes between an enhancer/delivery-aid transmissible form and an enhancer/delivery-aid non-transmissible form in response to said oscillations of said oscillation reaction.

9. The device of claim 1 wherein said active agent exists in a deliverable form and in a non-deliverable variation and converts between said deliverable form and non-deliverable variation as a result of interactions with one or more chemical species which are consumed or generated in the course of said oscillations of said oscillation reactions, where such interaction is other than a change of pH.

10. The device of claim 8, wherein said viscosity enhancer is a polymer selected from the group consisting of poly (meth)acrylates, cellulosics, alginates, chitosan, starches, hyaluronic acid, collagen, poly(ethylene oxides), poly (sulfonic acid), poly(acrylamide), poly(carboxylic acid), poly(hydroxylamine), poly(phosphonic acids), poly(amino acids), poly(vinyl alcohol), iodine-doped polymers, polyesters, polyamides, polyurethanes, cyclodextrins, non-ionic surfactants, gelatin gels, lecithin-ogranogels, ion exchange resins, polyelectrolytes, poly(hydroxamic acids), poly(3-carboxymethylpyrrole), borohydride exchange resins, oxidizing reagent polymers, and poly(N-vinyl-2-pyrrolidone).

11. The device of claim 8 wherein said barrier and said separation barrier are each independently selected from the group consisting of poly(siloxanes), poly(carboxylic acid), poly(sulfonic acid), poly(acylamide), poly(hydroxylamine), poly(phosphonic acids), poly(amino acids), poly(vinyl alcohol), and poly(N-vinyl-2-pyrrolidone), poly(meth) acrylates, cellulosics, alginates, chitosan, starches, hyaluronic acid, collagen, iodine-doped polymers, polyesters, polyamides, polyurethanes, ion exchange resins, polyelectrolytes, poly(hydroxamic acids), and poly(ethylene oxides).

12. The device of claim 1, comprising:
 a) a backing layer or laminate which is impermeable to the components of the device with which it comes in contact,
 b) a membrane or matrix layer through which the active agent must migrate,
 c) an oscillation reaction area in which an oscillation reaction can take place, once initiated,
 d) necessary oscillation reaction reactants; and
 e) an adhesive layer suitable for use in said transdermal device.

13. The device of claim 1 wherein at least one of said oscillation reaction reactants is added by a user or administrator of said device.

14. The device of claim 1 wherein all of said oscillation reaction reactants are present within said device, but at least two of said reactants are physically separated by a separation means so as to prevent said oscillation reaction from occurring, said device further comprising a means for modifying said physical separation by the action of a user or administrator of said device to allow said oscillation reaction to initiate.

* * * * *

UNITED STATES PATENT AND TRADEMARK OFFICE
CERTIFICATE OF CORRECTION

PATENT NO. : 6,068,853
DATED : May 30, 2000
INVENTOR(S) : Giannos et al.

Page 1 of 1

It is certified that error appears in the above-identified patent and that said Letters Patent is hereby corrected as shown below:

<u>Column 21, claim 2,</u>
Lines 42, 46, and 47 "oscillating" should read -- oscillation --.

Signed and Sealed this

Eighteenth Day of September, 2001

Attest:

*Nicholas P. Godici*

NICHOLAS P. GODICI
*Attesting Officer*     *Acting Director of the United States Patent and Trademark Office*